(12) United States Patent
Hinman et al.

(10) Patent No.: US 7,828,808 B2
(45) Date of Patent: Nov. 9, 2010

(54) LINK SYSTEMS AND ARTICULATION MECHANISMS FOR REMOTE MANIPULATION OF SURGICAL OR DIAGNOSTIC TOOLS

(75) Inventors: Cameron Dale Hinman, Woodside, CA (US); David J. Danitz, San Jose, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 118 days.

(21) Appl. No.: 10/928,479

(22) Filed: Aug. 26, 2004

(65) Prior Publication Data

US 2005/0273084 A1  Dec. 8, 2005

Related U.S. Application Data

(60) Provisional application No. 60/577,757, filed on Jun. 7, 2004.

(51) Int. Cl.
*A61B 17/00* (2006.01)
(52) U.S. Cl. .......................................... 606/108; 606/1
(58) Field of Classification Search .................. 600/141, 600/148; 604/528; 606/1, 108, 141
See application file for complete search history.

(56) References Cited

U.S. PATENT DOCUMENTS

| | | | | |
|---|---|---|---|---|
| 443,769 | A | * | 12/1890 | Hurford ..................... 474/211 |
| 1,820,463 | A | | 8/1931 | Klein |
| 3,060,972 | A | | 10/1962 | Sheldon |
| 3,071,161 | A | | 1/1963 | Ulrich |
| 3,190,286 | A | * | 6/1965 | Stokes ......................... 600/141 |
| 3,557,780 | A | | 1/1971 | Sato |
| 3,605,725 | A | | 9/1971 | Bentov |
| 4,466,649 | A | | 8/1984 | Ozawa |
| 4,489,826 | A | | 12/1984 | Dubson |
| 4,580,551 | A | | 4/1986 | Siegmund et al. |
| 4,700,693 | A | | 10/1987 | Lia et al. |
| 4,763,669 | A | | 8/1988 | Jaeger |
| 4,790,294 | A | * | 12/1988 | Allred et al. ................. 600/141 |
| 4,834,761 | A | | 5/1989 | Walters |
| 4,854,626 | A | | 8/1989 | Duke |
| 4,880,015 | A | | 11/1989 | Nierman |
| 4,984,951 | A | | 1/1991 | Jameson |

(Continued)

FOREIGN PATENT DOCUMENTS

EP   0 165 718   12/1985

(Continued)

OTHER PUBLICATIONS

U.S. Appl. No. 10/948,911, filed Sep. 24, 2004 for Danitz et al., 52 pages.

(Continued)

*Primary Examiner*—Anhtuan T Nguyen
*Assistant Examiner*—Ryan J Severson
(74) *Attorney, Agent, or Firm*—Shay Glenn LLP

(57) ABSTRACT

Articulating mechanisms, link systems, and components thereof, useful for a variety of purposes including, but not limited to, the remote manipulation of instruments such as surgical or diagnostic instruments or tools are provided. The link systems include links wherein at least two adjacent links are pivotable relative to one another around two distinct pivot points. Mechanisms for locking the links are also provided.

55 Claims, 22 Drawing Sheets

U.S. PATENT DOCUMENTS

| | | |
|---|---|---|
| 5,174,276 A * | 12/1992 | Crockard .................... 600/104 |
| 5,257,618 A | 11/1993 | Kondo |
| 5,271,381 A | 12/1993 | Ailinger et al. |
| 5,273,026 A | 12/1993 | Wilk |
| 5,286,228 A | 2/1994 | Lee et al. |
| 5,297,443 A * | 3/1994 | Wentz ................... 74/490.04 |
| 5,314,424 A | 5/1994 | Nicholas |
| 5,322,064 A | 6/1994 | Lundquist |
| 5,325,845 A | 7/1994 | Adair |
| 5,330,502 A | 7/1994 | Hassler et al. |
| 5,354,162 A | 10/1994 | Burdea et al. |
| 5,381,782 A | 1/1995 | DeLaRama et al. |
| 5,403,342 A | 4/1995 | Tovey et al. |
| 5,405,344 A | 4/1995 | Williamson et al. |
| 5,425,743 A | 6/1995 | Nicholas |
| 5,441,494 A | 8/1995 | Ortiz |
| 5,454,827 A | 10/1995 | Aust et al. |
| 5,476,479 A | 12/1995 | Green et al. |
| 5,486,154 A | 1/1996 | Kelleher |
| 5,490,819 A | 2/1996 | Nicholas et al. |
| 5,498,256 A | 3/1996 | Furnish |
| 5,520,678 A | 5/1996 | Heckele et al. |
| 5,522,788 A | 6/1996 | Kuzmak |
| 5,549,636 A | 8/1996 | Li |
| 5,562,699 A | 10/1996 | Heimberger et al. |
| 5,570,919 A | 11/1996 | Eusebe |
| 5,599,151 A * | 2/1997 | Daum et al. .................... 414/7 |
| 5,609,601 A | 3/1997 | Kolesa et al. |
| 5,620,415 A | 4/1997 | Lucey et al. |
| 5,624,398 A | 4/1997 | Smith et al. |
| 5,626,608 A | 5/1997 | Cuny et al. |
| 5,632,432 A | 5/1997 | Schulze et al. |
| 5,643,294 A | 7/1997 | Tovey et al. |
| 5,647,743 A | 7/1997 | Schmitt |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,759,151 A | 6/1998 | Sturges et al. |
| 5,792,164 A | 8/1998 | Lakatos et al. |
| 5,807,376 A | 9/1998 | Viola et al. |
| 5,813,813 A | 9/1998 | Daum et al. |
| 5,823,066 A | 10/1998 | Huitema et al. |
| 5,827,323 A | 10/1998 | Klieman et al. |
| 5,836,960 A | 11/1998 | Kolesa et al. |
| 5,846,183 A | 12/1998 | Chilcoat |
| 5,873,817 A * | 2/1999 | Kokish et al. ................ 600/143 |
| 5,899,425 A | 5/1999 | Corey, Jr. et al. |
| 5,916,146 A * | 6/1999 | Allotta et al. ................ 600/141 |
| 5,916,147 A | 6/1999 | Boury |
| 5,921,956 A | 7/1999 | Grinberg et al. |
| 5,938,678 A | 8/1999 | Zirps et al. |
| 5,961,532 A | 10/1999 | Finley et al. |
| 6,019,722 A | 2/2000 | Spence et al. |
| 6,050,996 A | 4/2000 | Schmaltz et al. |
| 6,161,543 A | 12/2000 | Cox et al. |
| 6,250,532 B1 | 6/2001 | Green et al. |
| 6,270,453 B1 | 8/2001 | Sakai |
| 6,446,850 B2 | 9/2002 | Ming-Shun |
| 6,464,704 B2 | 10/2002 | Schmaltz et al. |
| 6,471,641 B2 | 10/2002 | Sakamoto |
| 6,471,696 B1 | 10/2002 | Berube et al. |
| 6,482,149 B1 | 11/2002 | Torii |
| 6,491,626 B1 | 12/2002 | Stone et al. |
| 6,571,042 B1 * | 5/2003 | Kordahi .................... 385/100 |
| 6,626,824 B2 | 9/2003 | Ruegg et al. |
| 6,635,071 B2 | 10/2003 | Boche et al. |
| 6,638,213 B2 | 10/2003 | Ogura et al. |
| 6,638,287 B2 | 10/2003 | Danitz et al. |
| RE38,335 E | 11/2003 | Aust et al. |
| 6,641,528 B2 | 11/2003 | Torii |
| 6,644,532 B2 | 11/2003 | Green et al. |
| 6,666,854 B1 | 12/2003 | Lange |
| 6,669,254 B2 | 12/2003 | Thom et al. |
| 6,676,676 B2 | 1/2004 | Danitz et al. |
| 6,682,541 B1 | 1/2004 | Gifford et al. |
| 6,743,239 B1 | 6/2004 | Kuehn et al. |
| 6,746,443 B1 | 6/2004 | Morley et al. |
| 6,749,560 B1 | 6/2004 | Konstorum et al. |
| 6,752,823 B2 | 6/2004 | Prestel |
| 6,764,445 B2 | 7/2004 | Ramans et al. |
| 6,773,327 B1 | 8/2004 | Felice et al. |
| 6,817,972 B2 | 11/2004 | Snow |
| 6,824,548 B2 | 11/2004 | Smith et al. |
| 6,843,794 B2 | 1/2005 | Sixto, Jr. et al. |
| 6,858,005 B2 | 2/2005 | Ohline et al. |
| 6,902,560 B1 | 6/2005 | Morley et al. |
| 6,942,613 B2 | 9/2005 | Ewers et al. |
| 6,945,979 B2 | 9/2005 | Kortenbach et al. |
| 6,960,162 B2 | 11/2005 | Saadat et al. |
| 6,960,163 B2 | 11/2005 | Ewers et al. |
| 6,976,969 B2 | 12/2005 | Messerly |
| 6,994,700 B2 | 2/2006 | Elkins et al. |
| 7,138,976 B1 | 11/2006 | Bouzit et al. |
| 2001/0023313 A1 | 9/2001 | Ide |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto |
| 2003/0036748 A1 | 2/2003 | Cooper et al. |
| 2003/0050649 A1 | 3/2003 | Brock et al. |
| 2003/0078644 A1 | 4/2003 | Phan |
| 2003/0109898 A1 | 6/2003 | Schwarz et al. |
| 2003/0114838 A1 | 6/2003 | O'Neill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0138700 A1 | 7/2004 | Cooper et al. |
| 2004/0236316 A1 | 11/2004 | Danitz et al. |
| 2005/0090809 A1 | 4/2005 | Cooper et al. |
| 2005/0096694 A1 | 5/2005 | Lee |
| 2005/0107667 A1 | 5/2005 | Danitz et al. |
| 2005/0119527 A1 | 6/2005 | Banik et al. |
| 2005/0251112 A1 | 11/2005 | Danitz et al. |
| 2005/0273085 A1 | 12/2005 | Hinman et al. |
| 2006/0009759 A1 | 1/2006 | Christian et al. |
| 2006/0020287 A1 | 1/2006 | Lee et al. |
| 2006/0058582 A1 | 3/2006 | Maahs et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |

FOREIGN PATENT DOCUMENTS

| | | |
|---|---|---|
| EP | 0 598 618 A2 | 5/1994 |
| EP | 0 836 833 A2 | 4/1998 |
| EP | 0 836 833 A3 | 4/1998 |
| EP | 1 132 041 A2 | 9/2001 |
| EP | 1 395 398 B1 | 3/2004 |
| WO | WO98/49961 A1 | 11/1998 |
| WO | WO 01/10292 A1 | 2/2001 |
| WO | WO-02/13682 A1 | 2/2002 |
| WO | WO-2004/019769 A1 | 3/2004 |
| WO | WO-2004/105578 A2 | 12/2004 |
| WO | WO 2004/105578 A2 | 12/2004 |
| WO | WO-2004/105578 A3 | 12/2004 |
| WO | WO-2004/105578 C2 | 12/2004 |

| | | |
|---|---|---|
| WO | WO 2005/067785 A1 | 7/2005 |
| WO | WO-2005/120326 A2 | 12/2005 |
| WO | WO-2005/120326 A3 | 12/2005 |
| WO | WO-2005/120327 A2 | 12/2005 |
| WO | WO-2005/120327 A3 | 12/2005 |
| WO | WO-2006/057699 A1 | 6/2006 |
| WO | WO-2006/057700 A1 | 6/2006 |
| WO | WO-2006/057702 A2 | 6/2006 |
| WO | WO 2006/073581 A1 | 7/2006 |

OTHER PUBLICATIONS

U.S. Appl. No. 10/997,372, filed Nov. 23, 2004 for Danitz et al., 78 pages.
U.S. Appl. No. 11/344,465, filed Jan. 30, 2006 for Danitz, 28 pages.
Hegeman et al; U.S. Appl. No. 11/787,543 entitled "Tool with articulation lock," filed Apr. 16, 2007.
Hinman, Cameron; U.S. Appl. No. 11/787,607 entitled "Tool with rotation lock," filed Apr. 16, 2007.
Hinman, Cameron; U.S. Appl. No. 11/787,605 entitled "Tool with multi-state ratcheted end effector," filed Apr. 16, 2007.
Hinman et al; U.S. Appl. No. 11/787,599 entitled "Tool with end effector force limiter," filed Apr. 16, 2007.
Hegeman at al; U.S. Appl. No. 11/787,201 entitled "Articulating tool with improved tension member system" filed Apr. 16, 2007.
Danitz et al.; U.S. Appl. No. 12/109,333 entitled "Articulating instrument," filed Apr. 24, 2008.
Isbell Jr., Lewis; U.S. Appl. No. 12/542,589 entitled "Instrument with articulation lock," filed Aug. 17, 2009.
Hinman, Cameron; U.S. Appl. No. 12/508,478 entitled "Articulating mechanism," filed Jul. 23, 2009.

* cited by examiner

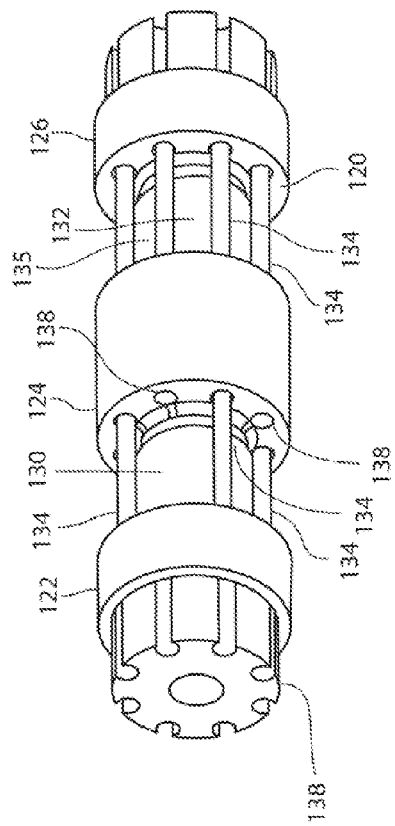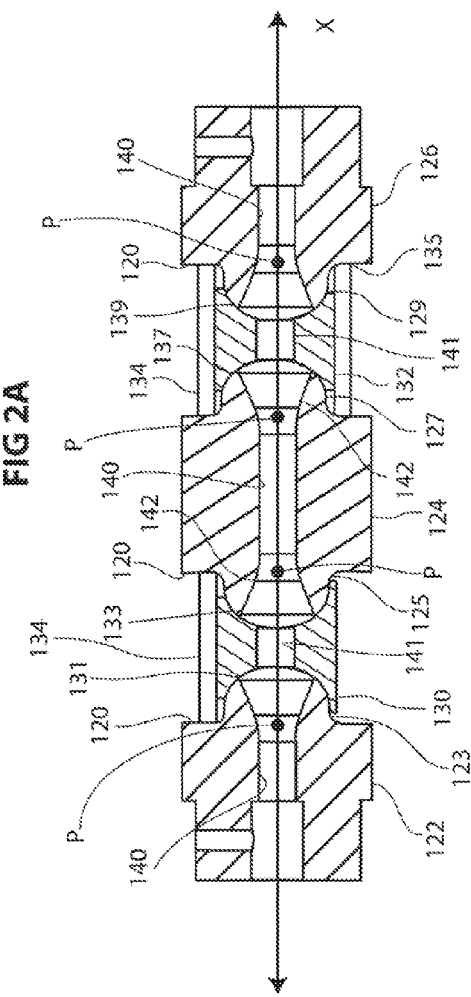

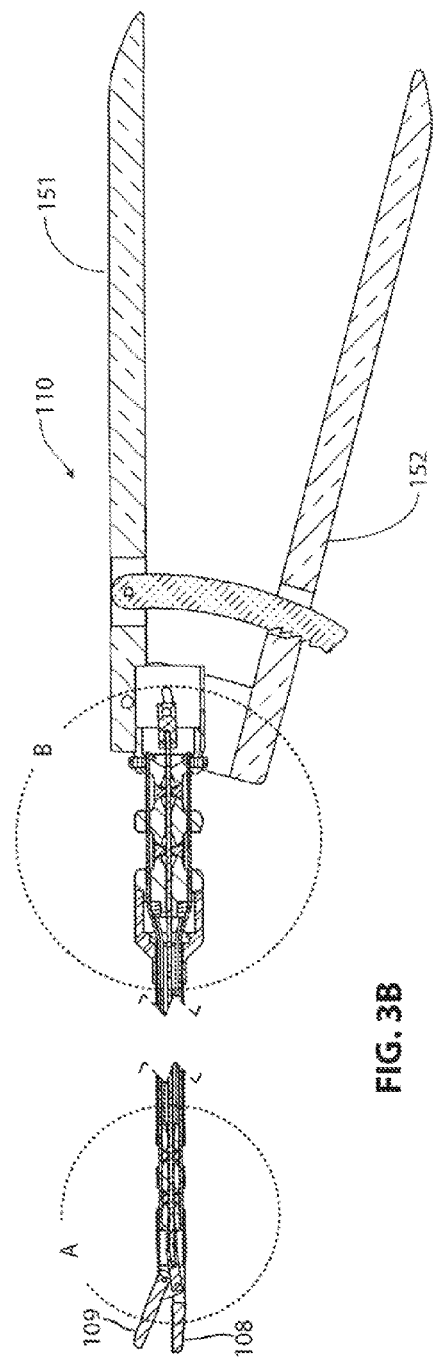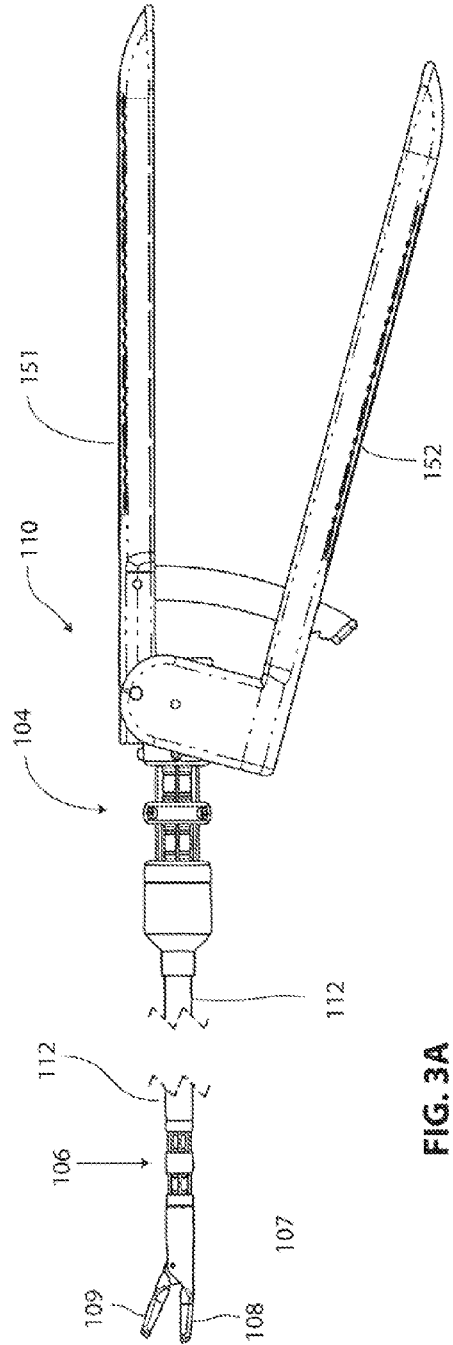
FIG. 3B
FIG. 3A

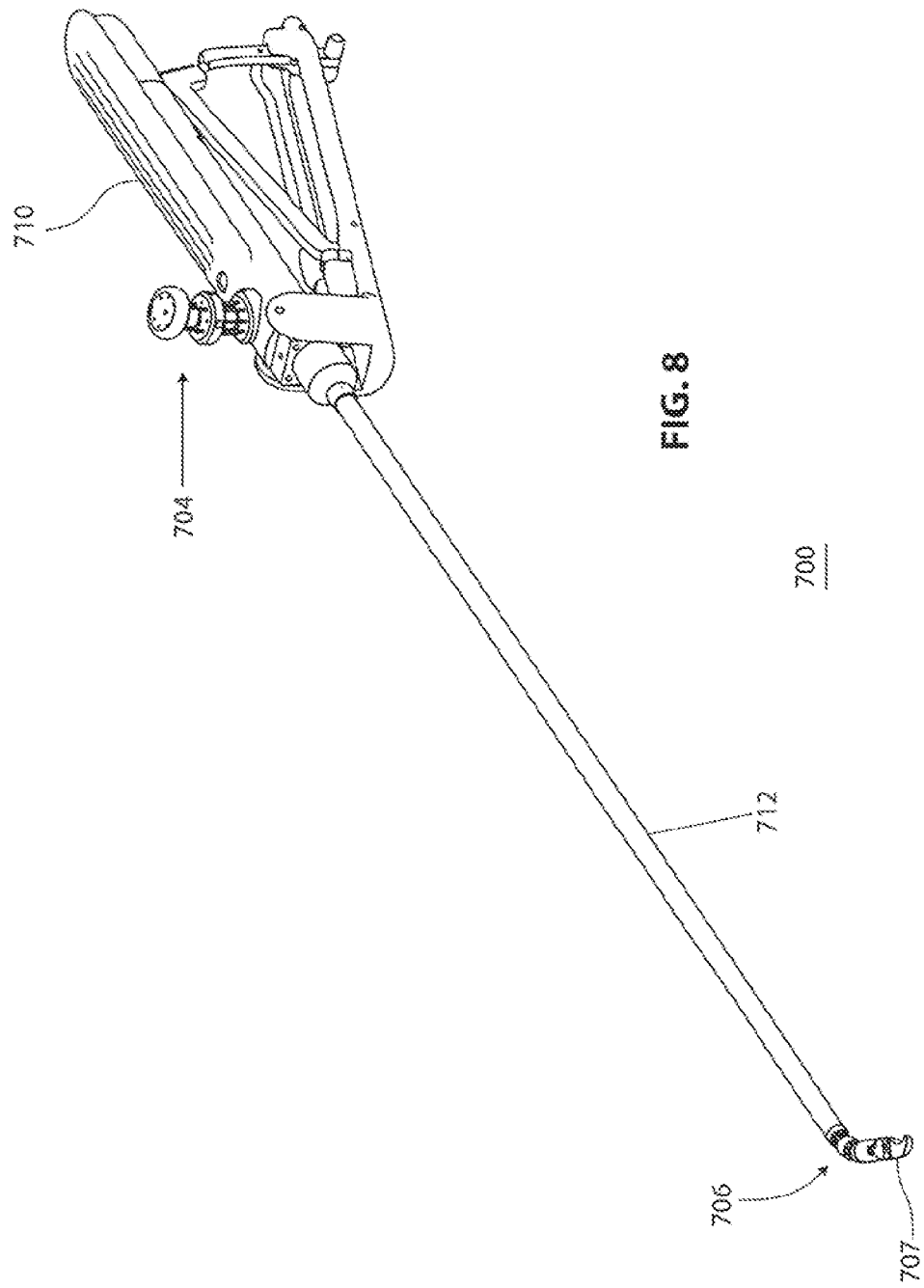

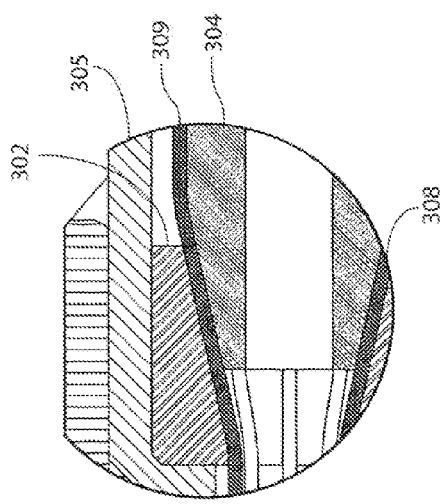
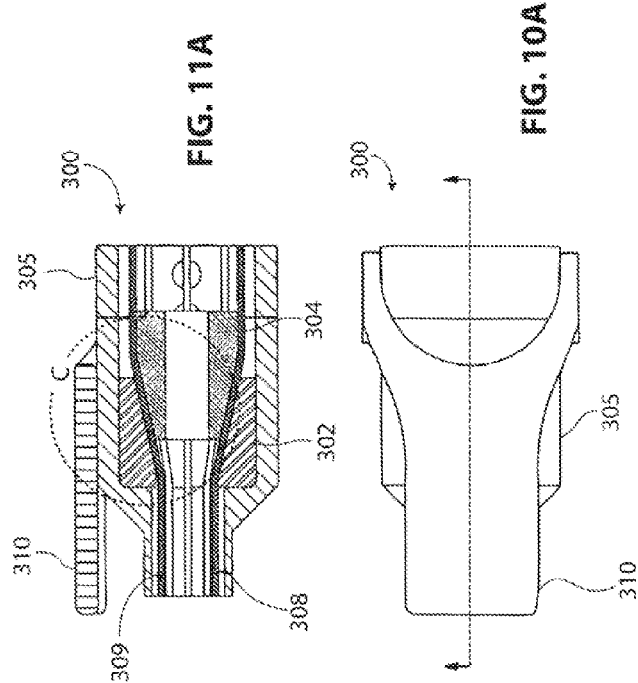
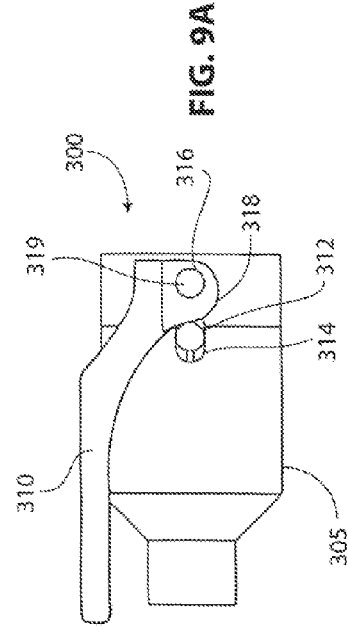

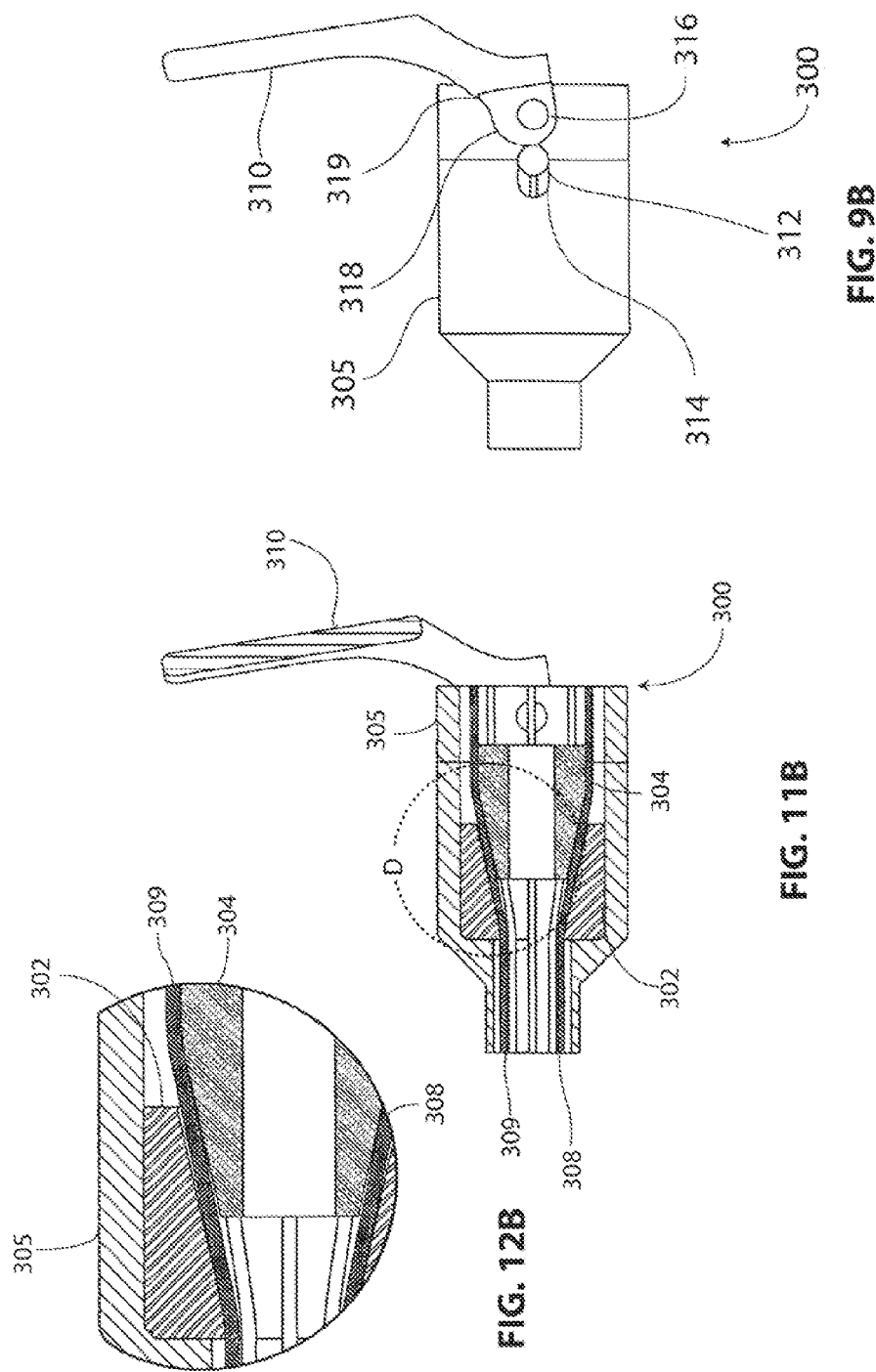

LINK SYSTEMS AND ARTICULATION MECHANISMS FOR REMOTE MANIPULATION OF SURGICAL OR DIAGNOSTIC TOOLS

CROSS-REFERENCE TO RELATED APPLICATION

This application claims the benefit of U.S. Provisional Application No. 60/577,757, filed Jun. 7, 2004, the contents of which is hereby incorporated by reference into the present disclosure.

FIELD OF THE INVENTION

This invention relates to link systems and applications thereof, including the remote guidance and manipulation of surgical or diagnostic instruments and tools.

BACKGROUND

The ability to easily remotely steer, guide and/or manipulate instruments and tools is of interest in a wide variety of industries and applications, in particular where it is desired to navigate an instrument or tool into a workspace that is not easy to manually navigate by hand or that might otherwise present a risk or danger. These can include situations where the targeted site for the application of a tool or instrument is difficult to access, e.g. certain surgical procedures, or the manufacture or repair of machinery, or even commercial and household uses, where manual access to a targeted site is restricted or otherwise. Other situations can include e.g. industrial applications where the work environment is dangerous to the user, for example, workspaces exposed to dangerous chemicals. Still other situations can include e.g. law enforcement or military applications where the user may be at risk, such as deployment of a tool or instrument into a dangerous or hostile location.

Using surgical procedures as an illustrative example, procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy. Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues. Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures. Steerable catheters are also well known for both diagnostic and therapeutic applications. Similar to endoscopes, such catheters include tips that can be directed in generally limited ranges of motion to navigate a patient's vasculature.

There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato). U.S. Pat. No. 5,916,147 to Boury et al. discloses a steerable catheter having four wires that run within the catheter wall. Each wire terminates at a different part of the catheter. The proximal end of the wires extend loosely from the catheter so that the physician may pull them. The physician is able to shape and thereby steer the catheter by selectively placing the wires under tension.

Although each of the devices described above are remotely steerable, their range of motion is generally limited. The steering mechanisms may also be laborious to use, such as in the catheter of Boury et al. where each wire must be separately pulled to shape the catheter. Further, in the case of e.g. endoscopes and steerable catheters that use knob and pulley mechanisms, it requires a significant amount of training to become proficient in maneuvering the device through a patient's anatomy.

Consequently, a device with enhanced remote maneuverability to controllably navigate complex geometries may allow more efficient and precise advancement and deployment of instruments and tools. It would also be advantageous for such a device to provide a more intuitive and facile user interface to achieve such enhanced maneuverability. It would be further advantageous for such a device to limit undesired tension or slack in cable components. In addition, it would be advantageous for such a device to have a locking mechanism capable of preventing movement of the device. Such a device would have widespread application in guiding, steering and/or manipulating instruments and tools across numerous industries. Such a device would also of itself have entertainment, recreation and educational value.

BRIEF SUMMARY OF THE INVENTION

The present invention provides for articulating mechanisms, link systems, and components thereof, useful for a variety of purposes including, but not limited to, the remote manipulation of instruments such as surgical or diagnostic instruments or tools. Such instruments and tools can include surgical or diagnostic instruments or tools, including but not limited to endoscopes, catheters, Doppler flow meters, microphones, probes, retractors, dissectors, staplers, clamps, graspers, scissors or cutters, ablation or cauterizing elements, and the like. Other instruments or tools in non-surgical applications include but are not limited to graspers, drivers, power tools, welders, magnets, optical lenses and viewers, electrical tools, audio/visual tools, lasers, monitors, and the like. Depending on the application, it is contemplated that the articulating mechanisms, link systems, and other components of the present invention can be readily scaled to accommodate the incorporation of or adaptation to numerous instruments and tools. The link systems and articulating mechanism may be used to steer these instruments or tools to a desired target site, and can further be employed to actuate or facilitate actuation of such instruments and tools.

In one aspect of the invention, a link system is provided that includes a plurality of links, wherein at least two adjacent links are pivotable relative to one another about two distinct pivot points. In certain variations the adjacent links have opposing surfaces with each surface having an axially aligned convex protrusion or concave depression. In such variations, the link system further includes a bushing interposed between at least two adjacent links, the bushing contacting the convex protrusion or concave depression of each of the at least two adjacent links. The bushing may include a concave depression or convex protrusion configured to receive an opposing convex protrusion and/or concave depression of the adjacent links. In some instances, the convex protrusion or concave depression of adjacent links is hemispherical. Such link systems can be incorporated into or otherwise form components of articulating mechanisms according to the invention.

In another aspect of the invention, an articulating mechanism is provided for, e.g., remote manipulation of a surgical or diagnostic tool. The articulating mechanism can include one or more link systems that allow for remote manipulation of a distally located tool or instrument. In one variation, an articulating mechanism is provided that includes multiple pairs of links, each link being maintained in a spaced apart relationship relative to the other link of the pair. At least two adjacent links are pivotable relative to one another about two distinct pivot points. In certain variations the adjacent links have opposing surfaces each have an axially aligned convex protrusion or concave depression, and are separated by a bushing interposed therebetween. The articulating mechanism further includes multiple sets of cables, each set connecting the links of a discrete pair to one another such that movement of one link of a pair causes corresponding relative movement of the other link of the pair. In certain variations, the links are designed to reduce or eliminate excess cable slack or tension between adjacent links.

In a further aspect of the invention, a locking mechanism is provided that may be incorporated into an articulating mechanism. The mechanism is configured to receive one or more cables (or other actuating elements) distally connected to one or more links and, when activated, impede movement of the cables (or other actuating elements) thus impeding movement of the corresponding links themselves. In one embodiment of the locking mechanism, the mechanism is configured such that each cable is able to pass between a moveable locking member and a fixed contact member. Movement of the moveable locking member causes one or more cables to contact the fixed contact member thereby frictionally impeding the movement of one or more cables.

In another embodiment, the locking mechanism can include one or more locking channels positioned perpendicular to the central axis of the locking mechanism. A moveable button member is positioned in each of the one or more locking channels within the mechanism housing. The housing can include one or more through-channels that receive one or more cables (or other actuating elements), with each locking channel associated with each through-channel. Depression of the button member within the locking channel brings a cable (or other actuation elements) in an associated through-channel into frictional contact with the cylinder, thereby frictionally impeding movement of the cable.

In another embodiment, the locking mechanism includes a dual collar mechanism having axially aligned fixed and moveable collars. One or more cable sets (or other actuation elements) pass through one collar and around the perimeter of the other collar. Axial movement of the moveable collar towards the fixed collar brings the cables into contact with both collars, thereby frictionally impeding movement of the cables.

In a further aspect of the invention, a surgical device is provided that includes a surgical or diagnostic tool and a plurality of links proximal of the surgical or diagnostic tool. An elongate shaft is proximal of the plurality of links, and one or more cables are distally connected to one or more links and received proximally through the elongate shaft. Movement of one or more cables causes movement of one or more links. Again, at least two adjacent links are pivotable relative to one another about two distinct pivot points. In certain variations, at least two of the adjacent links have opposing surfaces with an axially aligned convex protrusion and/or concave depression and are separated by a bushing interposed therebetween. The bushing contacts the convex protrusion or concave depression of each of the adjacent links.

In further aspects of the invention, a tool or instrument may be attached to and extend from the link systems and/or articulating mechanisms, or the link systems and/or articulating mechanisms may be otherwise incorporated into such instruments or tools. In the case of surgical applications, examples of surgical or diagnostic tools include, but are not limited to, endoscopes, catheters, Doppler flow meters, microphones, probes, retractors, dissectors, staplers, clamps, graspers, scissors or cutters, and ablation or cauterizing elements. For other applications, numerous tools or instruments are likewise contemplated, including without limitation, e.g., graspers, drivers, power tools, welders, magnets, optical lenses and viewers, light sources, electrical tools, audio/visual tools, lasers, monitors, and the like. The types of tools or instruments, methods and locations of attachment, and applications and uses include, but are not limited to, those described in pending and commonly owned U.S. application Ser. No. 10/444,769, incorporated herein by reference in its entirety.

BRIEF DESCRIPTION OF THE DRAWINGS

FIG. 2A shows an expanded perspective view of a link system similar to the distal link system of the embodiment depicted in FIG. 1A, with adjacent links that include opposing axially aligned convex protrusions separated by a bushing interposed between the convex protrusions;

FIG. 2C shows a cross-sectional view of the link system shown in FIG. 2A, taken along the plane designated by line K-K;

FIG. 3A shows an expanded side view of the device depicted in FIG. 1 with parts broken away;

FIG. 3B shows an expanded cross-sectional view of the device depicted in FIG. 1 with parts broken away;

FIG. 8 shows a perspective view of a surgical needle driver instrument according to another embodiment of the invention, with the location of the distal links varied;

FIGS. 9A and 9B show a side view of a link locking mechanism according to another embodiment of the invention, in locked (9A) and unlocked (9B) positions, respectively;

FIG. 10A shows a top view of the locking mechanism of FIG. 9A;

FIGS. 11A and 11B show sectional views of the locking mechanism of FIG. 9A;

FIGS. 12A and 12B show expanded cross-sectional views of the locking mechanism of FIGS. 9A and 9B, designated by areas C and D, respectively;

DETAILED DESCRIPTION OF THE INVENTION

Figure 1A:
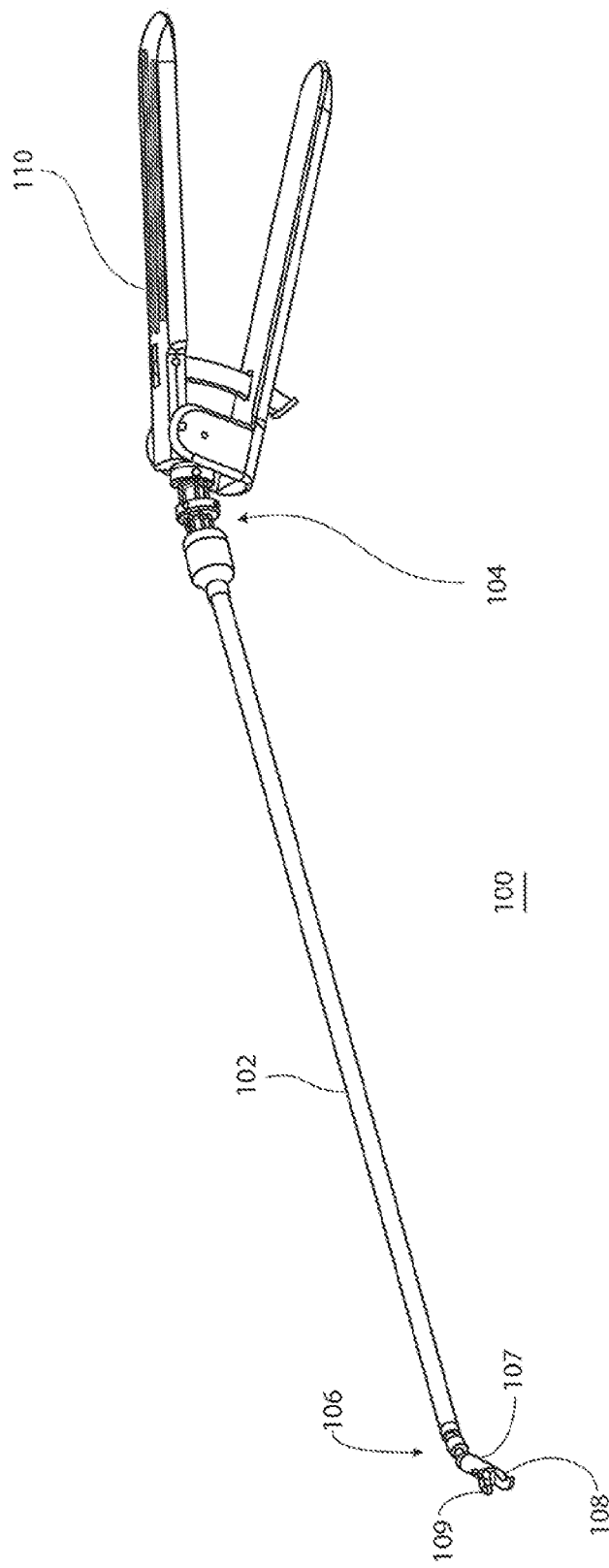
FIG. 1A shows a perspective view of a surgical needle driver device according to one embodiment of the invention, with proximal and distal articulating link systems.

As further detailed herein, articulating link systems and mechanisms are provided that can form, or be incorporated into, or otherwise constitute a wide variety of devices. The link systems may be made from a combination of individual links. Articulating mechanisms according to the invention generally include multiple pairs of links and at least one set of cables connecting at least one discrete pair of links. The term "link" as used herein refers to a discrete portion of a link system or articulating mechanism that is capable of movement relative to another discrete portion of the mechanism or system. In some embodiments, the link may correspond to another discrete portion or defined area at the opposite end of the mechanism. Links are typically, but need not be, cylindrical. The links are generally aligned along the longitudinal axis of the mechanism. In certain embodiments, the link systems will include a plurality of links, at least two of which are separated by a bushing.

The link systems can form or be incorporated into a variety of articulating mechanisms. In various embodiments, articulating mechanisms according to the invention generally include multiple pairs of links and multiple sets of cables. In further embodiments, the articulating mechanism includes a plurality of links or segments that are members of discrete pairs. The links form a proximal end and a distal end, with one link of each pair being situated in a link system at the proximal end, and the other link of the link pair in a link system at the distal end.

In such articulating mechanisms, each cable set connects the links of a discrete pair in the articulating mechanism to one another so that movement of one link of a pair causes a corresponding movement of the other link in the pair. As used herein, the term "active link" or "active link pair" refers to links that are directly connected to one another by a cable set. The term "spacer link" or "spacer link pair" refers to links that are not directly connected by a cable set. Spacer links can nevertheless be disposed between active links and provide for the passage of cable sets that connect active link. The ability to manipulate active link pairs allows for the mechanism to readily form complex three-dimensional configurations and geometries as is further detailed herein. With conventional articulating devices that rely on cable sets or wires that pass through otherwise unconnected links, it is difficult to obtain such complex geometries because such devices are typically designed such that the steering cables or wires pass through each link and terminate at a distal-most link. Thus, all the segments bend together in a coordinated response to movement of the wire or cable set, typically in a curved, or arcuate fashion.

The link systems or articulating mechanisms of the present invention may, for example, be incorporated into devices used to direct and steer a surgical or diagnostic instrument tool to a target site within a body region of a patient. The device can be introduced either in its native, straight configuration, or after undergoing various manipulations at its proximal end from a location outside the patient. In various embodiments, link systems form a part or parts of an articulating mechanism. Movement of the proximal end of the mechanism, results in movement at the distal end. Further, the resulting directional movement of the distal end can be inverted, mirrored or otherwise, depending on the degree of rotation of the proximal end relative to the distal end. Also, the proximal end provides for a user interface to control the steering and manipulation of the distal end that is convenient and easy to use. This user interface allows for example a user to readily visualize the shape and directional movement of distal end of the mechanism that is located e.g. within a patient based on the manipulated shape of the externally positioned proximal end user interface. Alternatively, control or actuation of the distal end links can be accomplished by more conventional methods of manipulating the link actuating cables, e.g., through the use of knob and pulley systems and the like.

In addition to the formation of complex configurations, the present invention also allows for increased rigidity of the mechanism by constraining manipulated active links and allowing such links to resist movement due to laterally applied forces. A given link pair is considered fully constrained if upon manipulating the links to achieve the desired shape, and fixing one link of the pair in that desired shape, the other link of the pair can resist loads while maintaining its desired, unloaded shape. For links that are otherwise free to move in three degrees of freedom, a minimum of three cables are required to fully constrain the links. This is not always the case with conventional articulating devices. Spacer links will not be so constrained, and the inclusion of such unconstrained links may be advantageous in many situations where it is desirable to have portions of the actuated mechanism be less rigid.

The terms "instrument" and "tool" are herein used interchangeably and refer to devices that are usually handled by a user to accomplish a specific purpose. For purposes of illustration only, link systems and articulating mechanisms of the invention will be described in the context of use for the remote guidance, manipulation and/or actuation of surgical or diagnostic tools and instruments in remote accessed regions of the body. As previously noted, other applications of the link systems and articulating mechanisms besides surgical or diagnostic applications are also contemplated and will be apparent to one of skill in the art. Generally any such application will include any situation where it is desirable to navigate an instrument or tool into a workspace that is not easy to manually navigate by hand or that might otherwise present a risk or danger. These include, without limitation, industrial uses, such as for the navigation of a tool, probe, sensor, etc. into a constricted space, or for precise manipulation of a tool remotely, for example, for the assembly or repair of machinery. These can also include commercial and household situations where the targeted site for the application of a tool or instrument is difficult to access. Other situations can include e.g. industrial applications where the work environment is dangerous to the user, for example, workspaces exposed to dangerous chemicals. Still other situations can include e.g. law enforcement or military applications where the user may be at risk, such as deployment of a tool or instrument into a dangerous or hostile location. Yet other uses include applications where simply remote manipulation of complex geometries is desirable. These include uses in recreation or entertainment, such as toys or games, e.g., for remote manipulations of puppets, dolls, figurines, and the like.

With reference to FIG. 1A, an embodiment of the invention is depicted which incorporates an articulating mechanism and link system according to the invention. As shown in FIG. 1A, needle driver 100 includes an articulating mechanism 102 having a proximal link set 104 and corresponding distal link set 106, separated by elongate shaft 112, which both maintains the proximal and distal link sets in a spaced apart relationship and also provides a working shaft for advancing the needle driver. Needle driver tool 107 with grasping jaws 108, 109 is attached to the distal end of distal link set 106 and is operationally connected to ratchet handle 110, which is attached to the proximal end of proximal link set 104. Needle driver 100 as configured is suitable for laparoscopic use. While this embodiment incorporates a needle driver tool, it will be readily appreciated that wide variety of surgical tools and instruments can be operationally attached to the distal end, including but not limited to a Doppler flow meter, microphone, endoscope, light source, probe, retractor, dissector, stapler, clamp, grasper, scissors or cutter, or ablation or cauterizing elements, as well as other tools or instruments for non-surgical applications, as has been previously noted.

As depicted in greater detail in FIGS. 3A-5, proximal and distal link sets 104 and 106 include corresponding pairs of links, i.e., each individual link in proximal link set 104 is paired with an individual link in distal link set 106 to form a series of discrete pairs. Distal link set 106 include links 122A, 124A, and 126A, while proximal link set 104 include links 122B, 124B, and 126B. Link 122A and 122B, 124A and 124B, and 126A and 126B are each discrete link pairs. The proximal links (122B, 124B, and 126B) are connected to the distal links (122A, 124A, and 126A) by sets of cables 134, 135 such that movement of proximal links in proximal link set 104 causes a corresponding relative movement of distal link set 106. In particular, links 122A and 122B are connected by cables 134, and links 124A and 124B are connected by cables 135, with links 126A and 126B affixed to elongate shaft 112. Links 122A and 122B, and links 124A and 124B, thus form active link pairs. Generally speaking, one or more sets of cables are used to connect active link pairs of an articulating mechanism according to varying embodiments of the invention. As previously noted, each active link at one end of an articulating mechanism is connected to its corresponding link at the other end by two or more cables that form a cable set. As noted, movement of one active link pair is controlled by its corresponding cable set and is independent of any other active link pair.

FIGS. 2A-D show a representation of a link set similar to link set 106 as separated from device 100 and in greater detail. As can be seen, adjacent links 122 and 124 are separated by a bushing 130, and adjacent links 124 and 126 are separated by a bushing 132. As more clearly seen in FIG. 2C, each link is aligned along longitudinal axis X1 of the link set with adjacent links 122 and 124 and adjacent links 124 and 126 each have opposing convex protrusions (123, 125, 127, 129) aligned along the axis. Each bushing 130 and 132 has opposing concave depressions (131, 133, 137, 139) for receiving the convex protrusions of links 122, 124, and 126. The links further include channels 138 that allow the passage of cable sets 134 and 135. Cable sets 134 and 135 are connected to links 122 and 124, respectively. The cable channels are offset from the central axis of the links such that when a tension force is applied to one or more cables, the convex protrusions of the links 122, 124, and 126 can rotate within the respective concave depressions of each bushing (130 and 132), thereby pivoting each link about a pivot point and allowing the link set as a whole to bend, as is shown more clearly in FIG. 2D. Each link and bushing also includes central channels 140 and 141 respectively that are aligned with the central axis of each link or bushing. When assembled, these channels form a central lumen through which an actuating cable (148) is passed for controlling and/or actuating the needle driver tool (107). The central channel generally also provide passage for additional cables, wires, fiberoptics or other like elements associated with any desired tool or instrument used in conjunction with the link system or articulating mechanism of the invention. The central channels of bushings 130 and 132 terminate in the shape of a conical frustum 142, as shown. This allows the links and bushings to pivot relative one another without impinging the passage of an actuating cable. The overall dimensions of the conical frustum portion generally will be commensurate with the degree of relative pivoting desired between the links and the bushings. While the provision of a central channel is advantageous for the above reasons, it will be appreciated that links and bushings can also be provided without such channels, and that control of tool or instrument associated with the link system or articulating mechanism of the invention can also be accomplished by routing actuating cables and other like elements along any radial location, including the periphery of the link system or articulating mechanism.

Turning to FIGS. 3A-5, device 100 as noted includes elongate shaft 112 disposed between proximal link sets 104 and distal links 106. The shaft is typically hollow and includes lumen 114 that accommodate both the cable sets 134 and 135 that connect the link pairs, as well as actuating cable 148. The shaft lumen generally provides passage for additional cables, wires, fiberoptics or other like elements associated with any desired tool or instrument used in conjunction with the link system or articulating mechanism of the invention.

Figure 5:
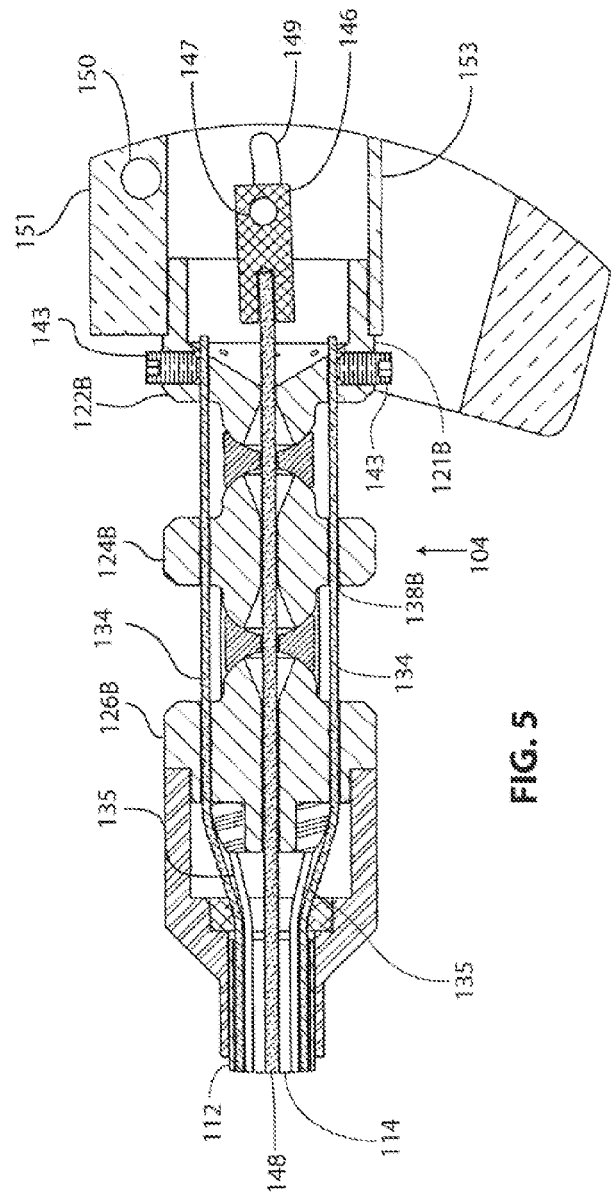
FIG. 5 shows a detailed cross-sectional view of the proximal link-handle assembly of the embodiment depicted in FIG. 3B, designated by area B.

Handle 110 of driver 100 is a conventional ratchet-style handle that is operably linked to actuating cable 148. In particular, as shown in FIGS. 3A, 3B and 5, handle 110 includes fixed arm 151 and pivoting arm 152, with arm 151 secured to proximal link 122B by collar 153 which engages reciprocal hub 121B of link 122B. Pivoting arm 152 is pivotally connected to fixed arm 151 at pivot 150, and further includes pin 147, which is received and translatable in guide slot 149 of arm 151. Actuating cable 148 terminates at it proximal end at the distal end of cable connector 146 which further receives pin 147 at its proximal end. When the handle 110 is actuated, arm 152 pivots around pivot point 150, thereby causing translational movement (i.e., rectraction) of the cable connector 146 and actuating cable 148 toward the proximal end of the device.

Figure 4:
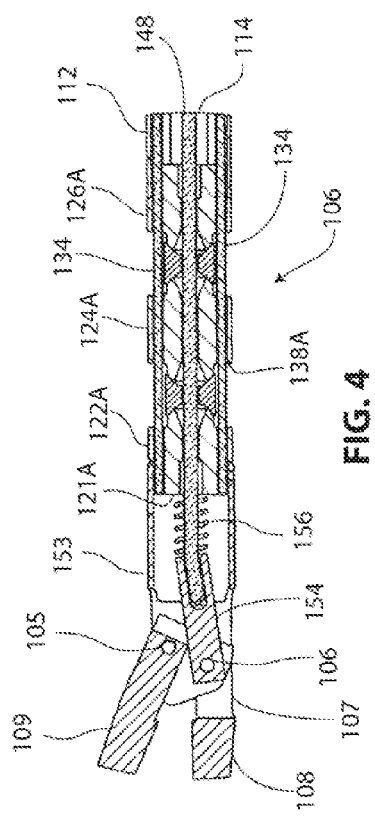
FIG. 4 shows a detailed cross-sectional view of the distal end tool and link assembly of the device depicted in FIG. 3B, designated by area A.

As most clearly shown in FIG. 4, needle driver 107 is similarly secured to distal link 122A by collar 153 which engages reciprocal hub portion 121A of link 122A. Jaws 108 and 109 extend distally with jaw 108 fixed and jaw 109 pivotally connected to jaw 108 at pivot 105. Cable connector 154 attaches to jaw 108 at its distal end at pin 106, and the distal end of actuating cable 148 is secured to the proximal end of cable connector 154. Spring 156 is disposed around cable 148 and between cable connector 154 and distal link 122A, keeping the cable in tension and jaw 109 in the open position, as shown. The needle driver is actuated by retraction of the central cable 148, which retracts connector 154 and compresses spring 156, causing pivotal movement of jaw 109 about pivot 105 into a closed position against jaw 108.

In various embodiments of the invention, the link sets or link systems are designed to have "neutral cable bias" based on the configuration of each link and bushing. When a link system bends due to an actuating force applied by a cable or cables along one side of the links, the relative tautness of cables passing through the links can be affected in a positive, negative or neutral manner. This effect, or bias, can also be referred to as "cable pull bias." Link systems that create or increase cable tension when the links are articulated are said to have "positive bias." Alternatively, link systems that result in decreased cable tension or slack when the links are articulated are referred to as having a "negative bias." Link systems that minimize cable tension and cable slack are said to have "neutral bias." Mechanisms that incorporate link systems with a neutral cable bias can generally retain their shape over a range of motion and resist counter forces applied against the mechanism that would compromise shape accuracy, and thus are generally preferred in most instances. However, depending on the application, negative or positive bias or effect can be advantageous. For example, in certain applications, negative cable bias, which introduces cable slack, may be desirable as it will decrease the rigidity of the articulated links, and limit their resistance to counter forces deployed along the links. Certain examples where this could be desirable include navigation of the links through or around sensitive or fragile anatomical structures. In other applications, positive cable bias, which introduces increased cable tension, may be desirable, as it will increase the rigidity of the articulated links and further their resistance to applied counter forces. Such tension can also provide resistance against further bending or articulation of the links. Examples where this could be desirable include applications where it is important to guard against too much bending or "overbending" of the link system.

Figure 2B:
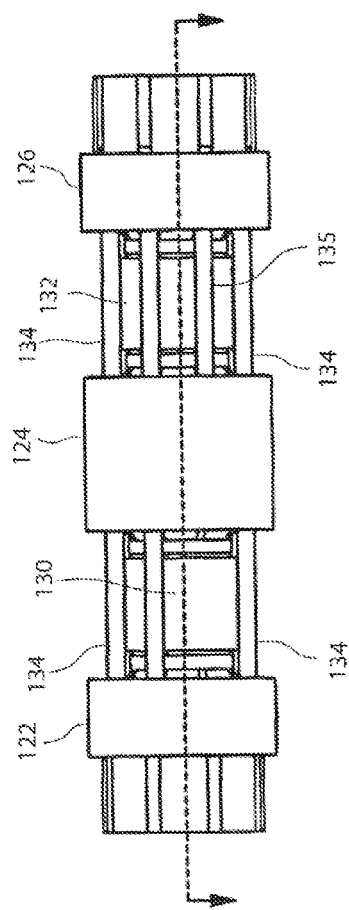
FIG. 2B shows a side view of the link system of FIG. 2A.
Figure 2D:
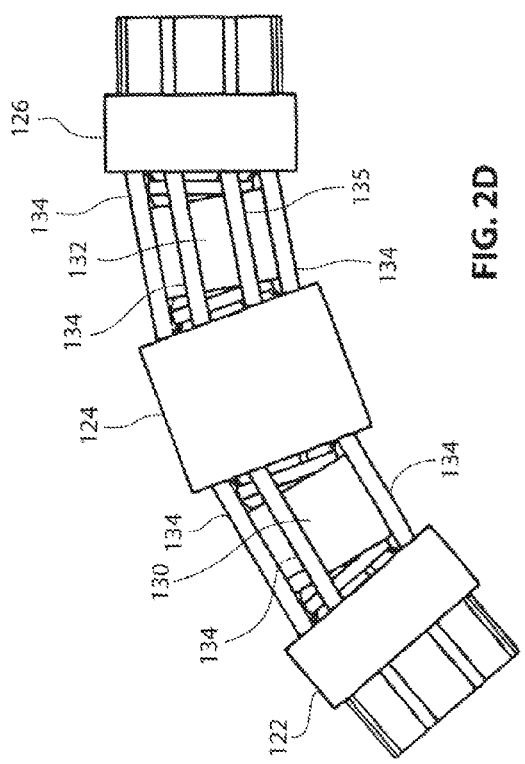
FIG. 2D shows a side view of the link system of FIG. 2A in a bent configuration.
Figure 2E:
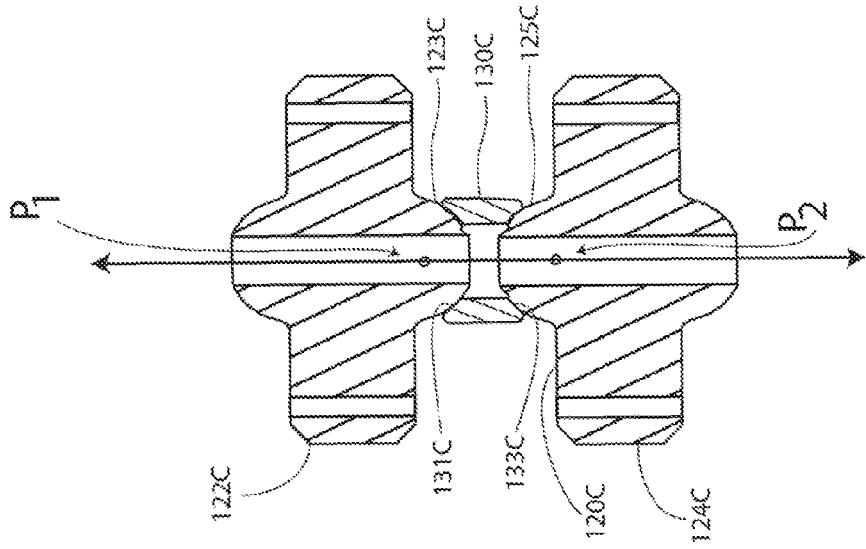
FIGS. 2E and 2F show straight and bent sectional views respectively, of a link system similar to that of FIG. 2A.
Figure 2F:
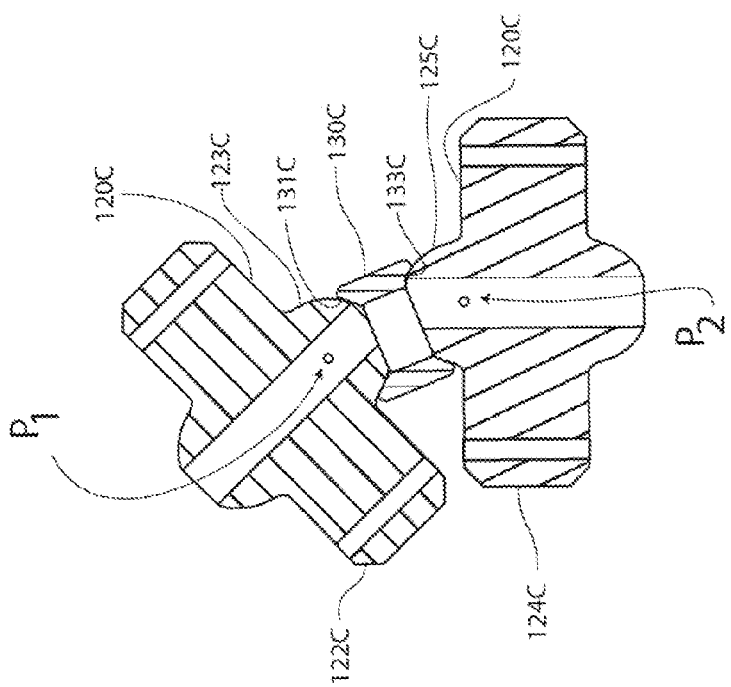

Referring again to FIGS. 2A-2D, the particular configuration of the links and bushings in link set 106 achieves neutral cable bias. Important to achieving neutral cable bias in this embodiment is the provision and location of the pivot points between each link-bushing-link assembly. Convex protrusions (123, 125, 127, 129) of the links 122, 124, and 126 are hemispherical, and concave depressions (131, 133, 137, 139) of the bushings 130 and 132 have a truncated hemispherical shape. The hemispherical shapes of the convex protrusions and concave depressions create pivot points P between adjacent links. The pivot points are located at the intersection of the central axis X of the link set and a plane defined by the flat, non-protruding axial face 120 of each link 122, 124, and 126, and correlate with the axis point around which the hemispherical convex protrusions are circumscribed. This is more clearly seen with reference to FIGS. 2E and 2F which show a link-bushing-link assembly similar in configuration to those shown in FIGS. 2A-2D. Here again links 122c and 124c are separated by bushing 130c. Link 122c and 124c include hemispherical protrusions 123c and 125c, respectively, that are received by truncated hemispherical depressions 131c and 133c of bushing 130c. This configuration again creates pivot points $P_1$, $P_2$ between the two links that are located at the intersection of axis X and planes defined by axial faces 120c of each link. The links otherwise have the same overall diameter, the corresponding cable channels have the same radius or distance from the link center, and the same distance or gap between adjacent links, as maintained by the interposed bushings.

When the links are manipulated into a desired position or configuration, each link of a link-bushing-link assembly pivots about its respective pivot point, such that any two adjacent links are pivoting toward or away from one another about dual pivot points. Further, as a result of such dual pivoting action for any given link, the distance a given cable channel exit point moves towards its corresponding cable channel exit point on an adjacent link is equal to the distance an opposing cable channel exit point on the opposite side of the link moves away from its corresponding cable channel exit point on the adjacent link. The combined distance between the two respective sets of cable channel exit points, however, remains constant whether or not the links are pivoted which is important to maintaining neutral cable bias. Where such combined distances are not equal, an increase in cable slack or tension can occur. Particularly, where the combined distance between sets of opposing channel exit points is greater when the links are pivoted or articulated as compared to the combined distance in the straight, non-articulated position, cable tension can occur. Alternatively, where the combined distance between sets of opposing channel exit points is lessened upon pivoting or articulation relative to a straight, non-articulated position, cable slack can occur.

Figure 21A:
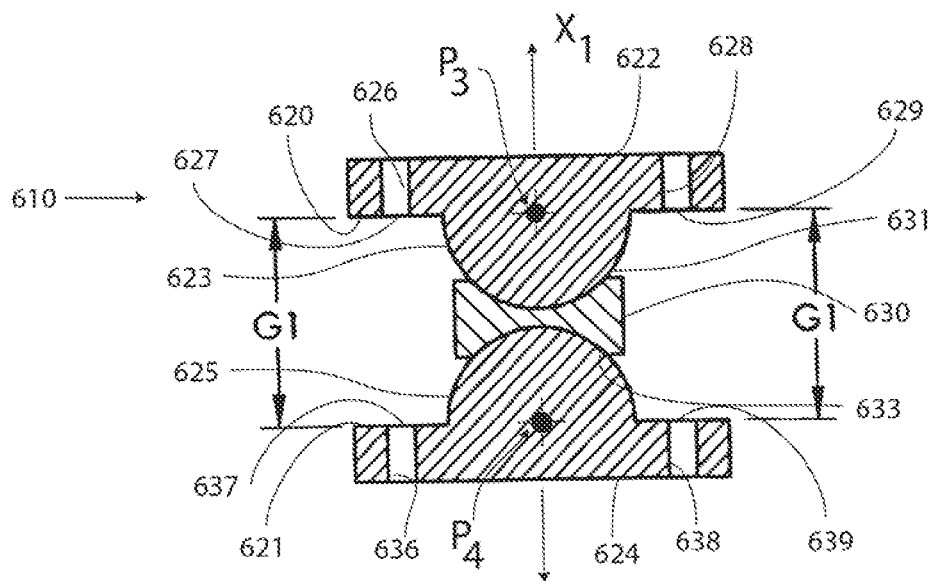
FIGS. 21A and 21B show straight and bent sectional views, respectively, of a link system according to another embodiment of the invention, configured for neutral cable bias.
Figure 21B:
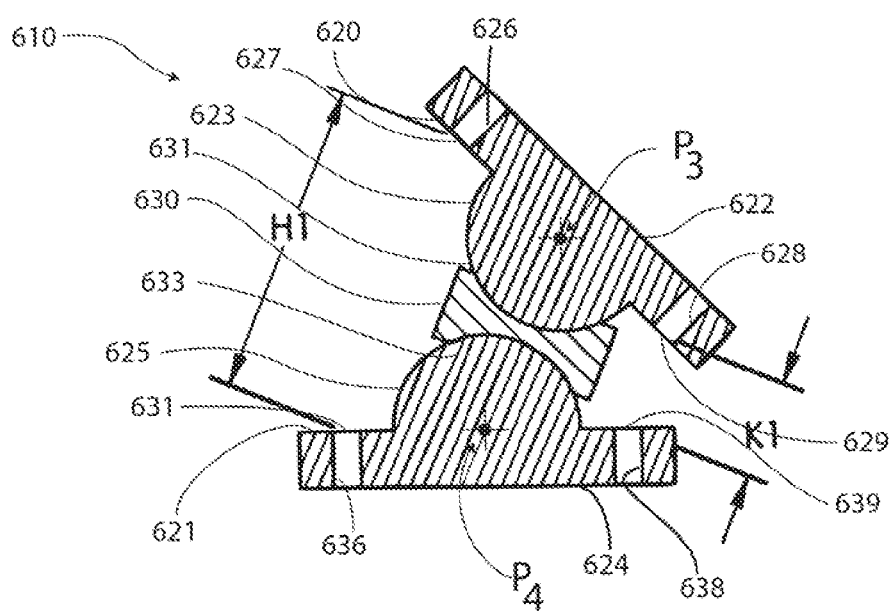

This phenomena is illustrated more clearly with reference to FIGS. 21A-23B, which show link assemblies (610, 640, 670) having neutral (FIGS. 21A-21B), negative (FIGS. 22A-22B), and positive (FIGS. 23A-23B) cable bias. Each link assembly (610, 640, 670) includes two adjacent links (622 and 624, 652 and 654, and 682 and 684) with a bushing (630, 660, 690) interposed between the two links. Similar to the above embodiments, the links include convex protrusions (623, 625, 653, 655, 683 and 685) that engage concave depressions (631, 633, 661, 663, 691, 693) of the bushings. Link assembly 610 of FIGS. 21A and 21B is configured similarly to the assembly shown in FIGS. 2E and 2F, and achieves neutral cable bias. Protrusions 623 and 625 are hemispherical and are received in depressions 631 and 633 that have a truncated hemispherical shape. As with the assemblies of FIGS. 2A-2F, this configuration also creates pivot points $P_3$ and $P_4$ located at the intersection of axis $X_1$ and the plane defined by the axial faces (620, 621) of the two links (622, 624), which coincide with cable channel exit points (627, 629, 637, 639) of cable channels (626, 628, 636, 638). As shown, exit points 627 and 629 of link 622 are on opposite sides of link 622 and are aligned with exit points 637 and 639 on adjacent link 624 when the assembly is in a straight, unbent position (FIG. 21A). In this position, the distance between exit points 627 and 637 and between 629 and 639 is the same, and is represented as G1 in FIG. 21A. When the assembly is bent (FIG. 21B), the relative distances between the corresponding exit points change, as represented by distances H1 and K1 in FIG. 21B. However, with the pivot positions $P_3$ and $P_4$ located as described above, the combined distance between opposing cable channel exit points remains the same as when the links are in the straight, unbent position. That is, G1+G1 is equivalent to H1+K1, which can be represented by the formula G1+G1=H1+K1.

Figure 22A:
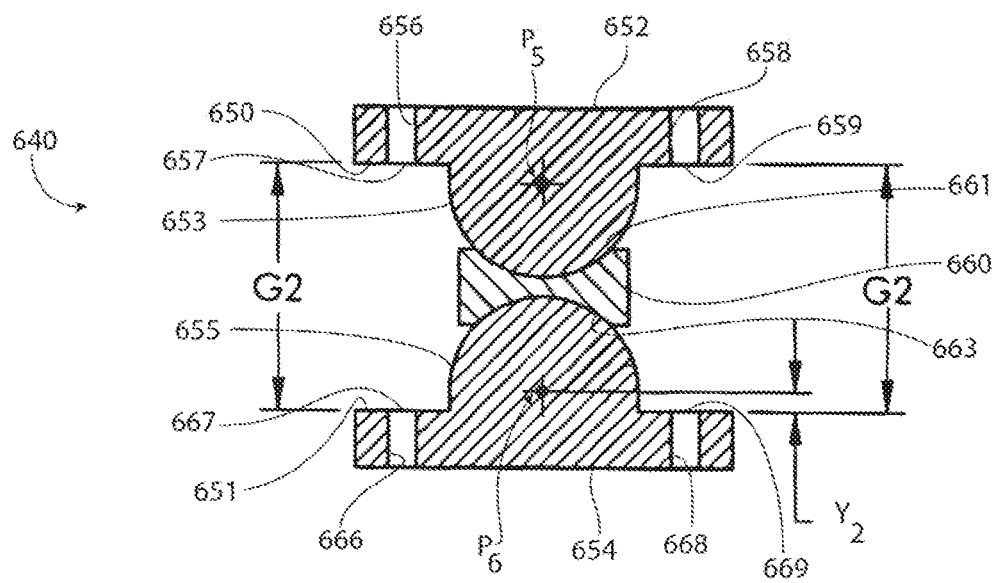
FIGS. 22A and 22B show straight and bent sectional views, respectively, of a link system according to yet another embodiment of the invention, configured for negative cable bias.
Figure 22B:
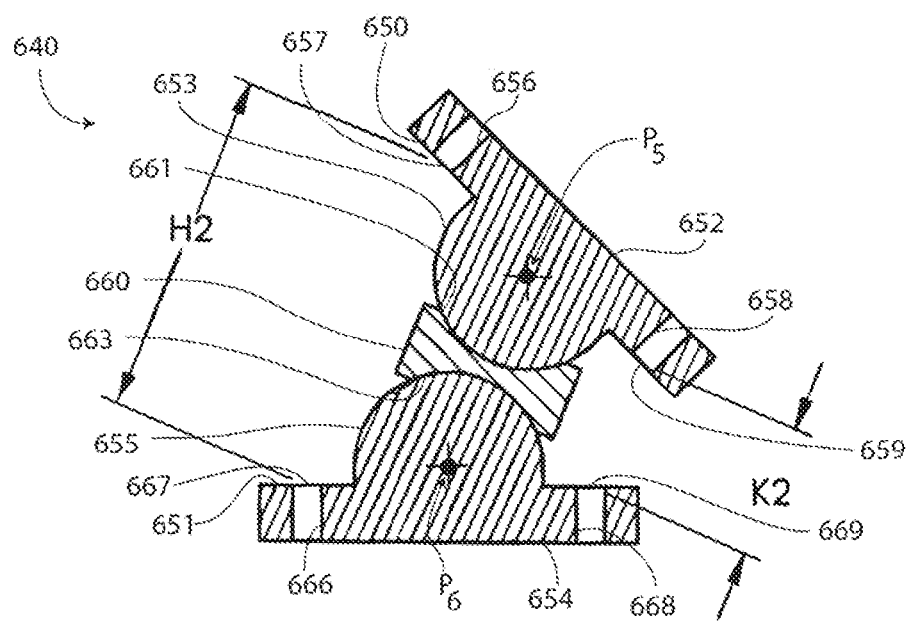
Figure 23A:
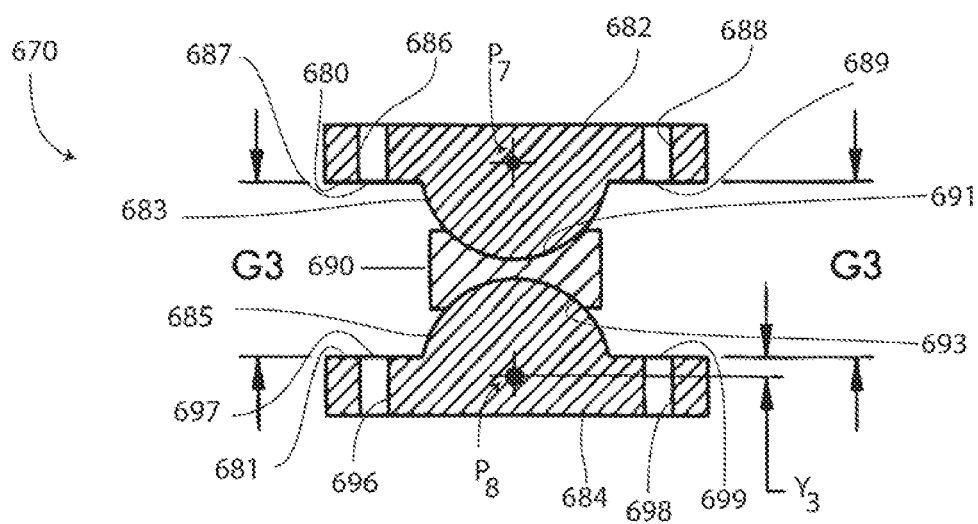
FIGS. 23A and 23B show straight and bent sectional views, respectively, of a link system according to a further embodiment of the invention, configured for positive cable bias.
Figure 23B:
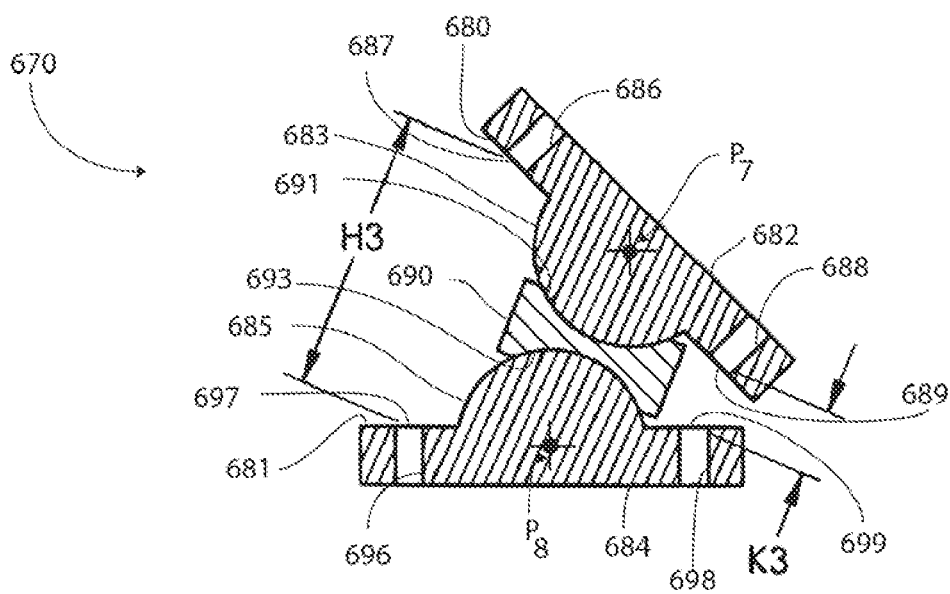

Link assembly 640 shown in FIGS. 22A-22B is designed to achieve negative cable bias, so as to increase cable slack upon articulation. The links and bushing of this assembly are the same as in FIGS. 21A-21B with the exception that links 652 and 654 have hemispherical tipped protrusions 653 and 655 that extend further from axial faces 650, 651 of links 652 and 654. As a result, pivot points $P_5$ and $P_6$ are created that no longer coincide with cable channel exit points 657, 659, 667, and 669 of cable channels 656, 658, 666, and 668, respectively. Instead, the pivot points are offset from the axial faces by a distance $y_2$ in a direction toward bushing 660. In this configuration, the combined distance between opposing cable channel exit points when pivoting occurs is not equal to the combined distance between the respective cable channel exit points when the links are in the straight, unbent position. That is, H2+K2 is not equal to G2+G2, but instead is a lesser value which results in the introduction of cable slack into the system. This can be represented by the formula G2+G2=H2+K2+Δ2, with the degree of cable slack introduced into the system correlating to the value Δ2.

Link assembly 670 (FIGS. 23A-23B) by contrast is designed to achieve positive cable bias which increases cable tension upon articulation. Again, the links and bushing of this assembly are the same as in FIGS. 21A-21B, but here the exception is that links 682 and 684 have convex protrusions 683 and 685 that are truncated hemispheres. This results in the establishment of pivot points $P_7$ and $P_8$ that are offset by a distance $y_3$ from the planes defined by axial faces 680, 681 of the links, but this time in a direction away from bushing 690. Here again, then, the pivot points do not coincide with cable channel exit points 687, 689, 697 and 699 of corresponding cable channels 686, 688, 696 and 698. Again, the combined distance between opposing cable channel exit points when pivoting occurs is not equal to the combined distance between the respective cable channel exit points in the straight, unbent position. Instead H3+K3 is greater than G3+G3, resulting in the introduction of cable tension into the system. This can be expressed as G3+G3=H3+K3−Δ3. Here the degree of cable tension introduced into the system again correlates to the value of Δ3.

Figure 6A:
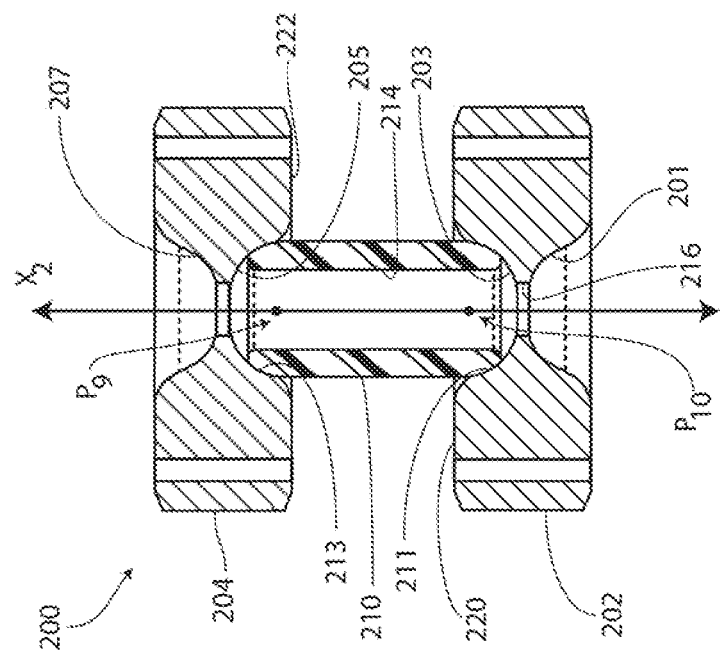
FIGS. 6A and 6B show straight and bent sectional views, respectively, of a link system according to another embodiment depicted in the invention, with adjacent links including opposing axially aligned concave sockets separated by a bushing interposed between the concave sockets.
Figure 6B:
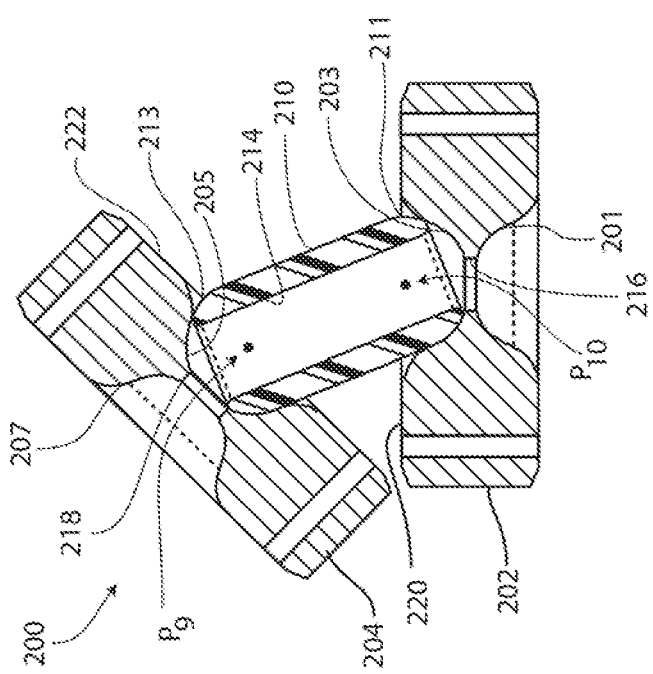

Neutral, negative, and positive cable bias can also be achieved in a variety of other link system conformations. By way of example and not limitation, the variation shown in FIGS. 6A and 6B, shows an alternative configuration of a link-bushing-link assembly that achieves similar dual pivoting and equidistant movement of cable channel exit points as does the FIGS. 2A-2D, 2E-2F, and 21A-21B links, and that also results in neutral cable bias. Link system 200 includes opposing adjacent links 202 and 204 separated by bushing 210. Adjacent links 202 and 204 each have opposing axially aligned hemispherical concave depressions (201, 203, 205, 207). Bushing 210 has truncated hemispherical convex protrusions 211, 213 for receiving the concave depressions 203 and 205 of each link 202 and 204, respectively. The link system has two pivot points $P_9$ and $P_{10}$ located at the intersection of the central axis $X_2$ of the link system and the planes defined by axial faces 220 and 222, respectively, of links 202 and 204 and that intersect the bushing 210 and that correlate with the axis points around which the truncated hemispherical convex protrusions of the bushing are circumscribed. The central channel 214 of bushing 210 has a larger diameter than the central channels 216, 218 of links 202 and 204, respectively, to allow for unimpeded passage of actuating cables, etc., when the links are pivoted, as can be seen in particular by reference to FIG. 6B. By modifying the assembly to introduce offset to the pivot point locations, positive or negative bias can be achieved.

Figure 7A:
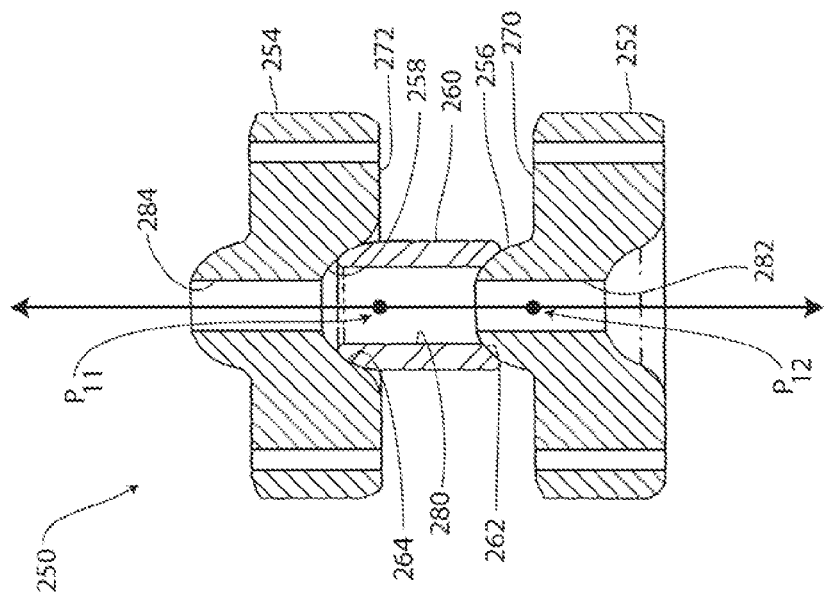
FIGS. 7A and 7B show straight and bent sectional views, respectively, of a link system according to yet another embodiment of the invention.
Figure 7B:
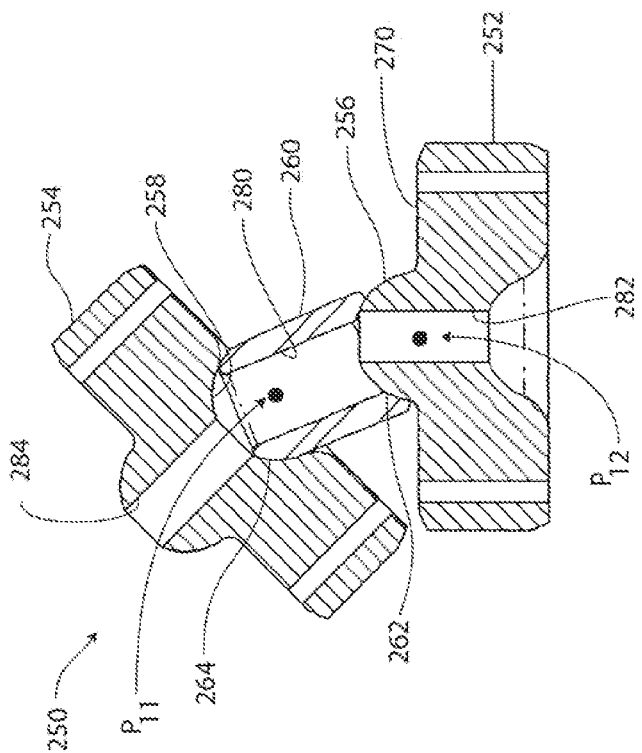
Figure 13:
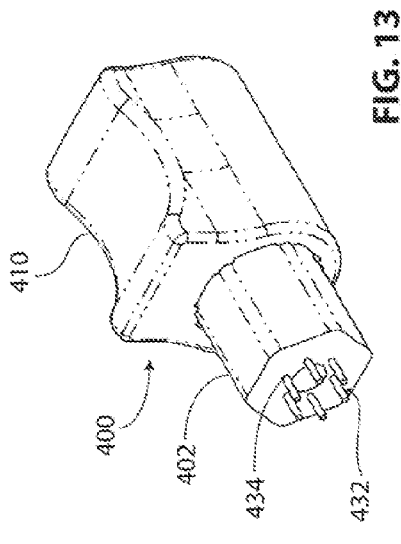
FIG. 13 shows a perspective view of a locking mechanism, according to another embodiment of the invention.
Figure 14:
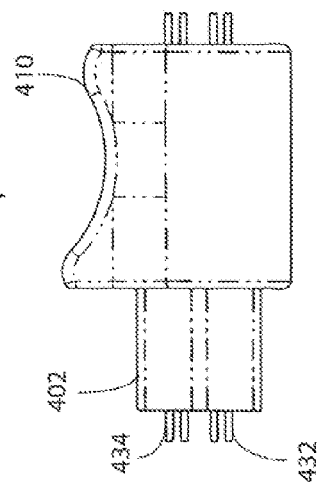
FIG. 14 shows a side view of the locking mechanism of FIG. 13.
Figure 15:
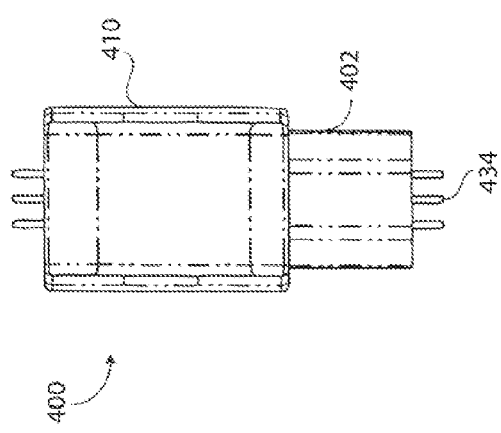
FIG. 15 shows a top view of the locking mechanism of FIG. 13.
Figure 16:
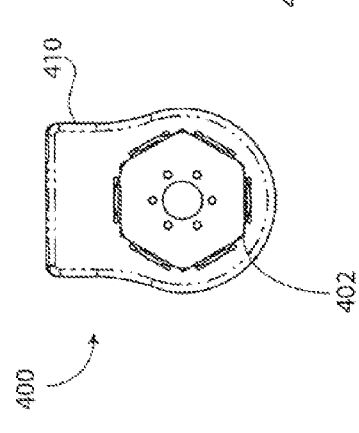
FIG. 16 shows an end view of the locking mechanism of FIG. 13.
Figure 17A:
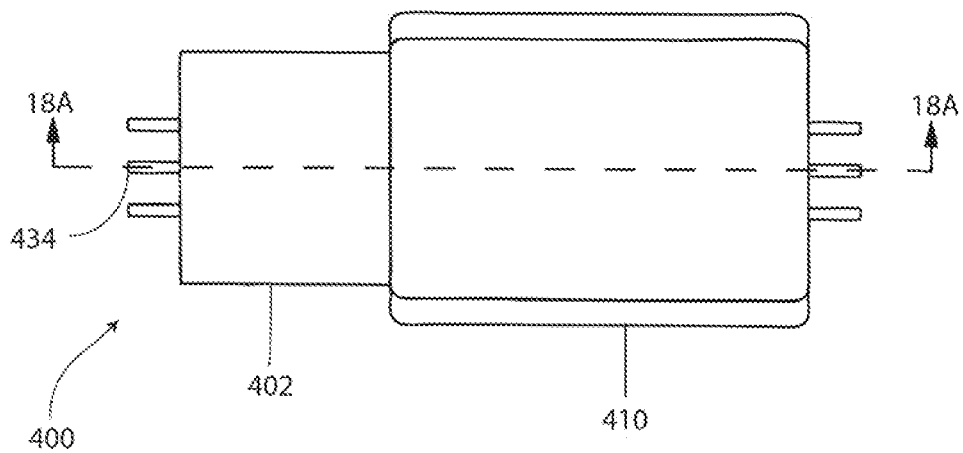
FIGS. 17A-17C show top views of the locking mechanism of FIG. 13, in unlocked (FIG. 17A) partially locked, (FIG. 17B) and locked positions (FIG. 17C)

Another link-bushing-link assembly is shown FIGS. 7A and 7B that likewise achieves neutral cable bias. The links of this system have both concave depressions and convex protrusions that engage a bushing interposed between the links. The bushing likewise has corresponding convex protrusions and concave depressions. This link-bushing-link assembly likewise achieves similar dual pivoting and equidistant movement of cable channel exit points as does the FIGS. 2A-2D links and FIGS. 6A and 6B links. Link system 250 includes opposing adjacent links 252 and 254 separated by bushing 260. Link 252 has a hemispherical convex protrusion 256, and link 254 has an opposing hemispherical concave depression 258 that is axially aligned with convex protrusion 256. Bushing 260 has a truncated hemispherical concave depression 262 that receives convex protrusion 256 of link 252, and a truncated hemispherical convex protrusion 264 that is received by concave depression 258. The link system 250 has two pivot points $P_{11}$ and $P_{12}$ located at the intersection of the central axis $X_3$ of the link system and the plane defined by either the flat, non-concave and non-convex axial face 270 of link 252, or the flat, non-concave and non-convex axial face 272 of link 254 that intersects bushing 260. These pivot points further correlate with the axis points around which convex hemispherical protrusion of the link or the truncated hemispherical convex protrusions of the bushing are circumscribed. The central channel 280 of bushing 260 has a larger diameter than the central channels 282, 284 of links 252 and 254, respectively, to allow for unimpeded passage of actuating cables, etc., when the links are pivoted, as can be seen in particular by reference to FIG. 7B. Again, by modifying the assembly to introduce offset pivot point locations, positive or negative bias can be achieved.

While particular embodiments of bushings have been described as having convex protrusions and/or concave depressions that are engaged with concave depressions and/or convex protrusions of corresponding links, bushings that are simply cylindrical and hollow with generally blunt ends are likewise useful. Such bushings will function equally well when engaged with the convex protrusions and/or concave depressions of the corresponding links, provided the inner diameter of the bushing is slightly smaller than the diameter of the corresponding convex protrusion, or alternatively the outer diameter of the bushing is slightly smaller than the corresponding concave depression, to allow for pivoting movement of the link relative to the bushing.

Consistent with the configurations and parameters otherwise discussed above, the links and bushings in the link systems and articulating mechanisms according to the invention may be of any size and shape, as the purpose dictates. For surgical applications, their form usually depends on such factors as patient age, anatomy of the region of interest, intended application, and surgeon preference. As noted, links and bushings are generally cylindrical, and may include channels for passage of the cables that connect links to other links or components of a device, as well as additional cables, wires, fiberoptics or other like elements associated with a desired tool or instrument used in conjunction with the link system. The channel diameters are usually slightly larger than the cable diameters, creating a slip fit. Further, the links may also include one or more channels for receiving elements of attachable surgical instruments or diagnostic tools or for passage of cables that actuate them. As noted, such channels can be located along the center or the periphery or at any radial location of the links or bushings. The links may typically have a diameter from about 0.5 mm to about 15 mm or more depending on the application. Bushings tend to have relatively comparable sizes to links, and frequently have a smaller diameter. For endoscopic applications, representative link diameters may range from about 2 mm to about 3 mm for small endoscopic instruments, about 5 mm to about 7 mm for mid-sized endoscopic instruments, and about 10 mm to about 15 mm for large endoscopic instruments. For catheter applications, the diameter may range from about 1 mm to about 5 mm. The overall length of the links and bushings will vary, usually depending on the bend radius desired between links.

For surgical applications, the links or bushings or other components of the mechanism or device into which the links or bushings are incorporated may be made from any biocompatible material including, but not limited to, stainless steel; titanium; tantalum; and any of their alloys; and polymers, e.g., polyethylene or copolymers thereof, polyethylene terephthalate or copolymers thereof, nylon, silicone, polyurethanes, fluoropolymers, poly (vinylchloride); and combinations thereof. A lubricious coating may be placed on the links or bushings or other components if desired to facilitate advancement of the link system. The lubricious coating may include hydrophilic polymers such as polyvinylpyrrolidone, fluoropolymers such as tetrafluoroethylene, or silicones. A radioopaque marker may also be included on one or more links or bushings to indicate the location of the articulating mechanism or device upon radiographic imaging. Usually, the marker will be detected by fluoroscopy.

Although the many link systems that have been illustrated in the accompanying figures have a certain number of links and bushings, this is solely for the illustrative purpose of indicating the relationship of the individual mechanism or link and bushing components to one another. Any number of links and bushings may be employed, depending on such factors as the intended use and desired length and range of movement of the articulating mechanism.

As noted, cables may be used to actuate the link systems of the invention. In such embodiments, one or more links are connected to its corresponding link or segment at the distal end by two or more cables. Each cable set may be made up of at least two cables. As noted, movement of one link is controlled by its corresponding cable set and is independent of any other link. In certain variations, for example, a cable set will include three cables. By using a set of three cables to connect to a link, the link can be manipulated or moved in three degrees of freedom (i.e., up/down motion, left/right motion, and rotational or "rolling" motion), independently of any other links. By combining a plurality of links, multiple degrees of freedom are achieved, allowing the link system to be shaped into various complex configurations. For example, the distal link set 106 shown in FIG. 2A has a total of three links (122, 124, 126) with two links (122, 124) independently connected by sets of cables (134, 135), for possible motion in six degrees of freedom. Such multiple degrees of freedom are not available in typical conventional mechanisms where only a single set of cables is employed to manipulate the links.

Cable diameters vary according to the application, and may range from about 0.15 mm to about 3 mm. For catheter applications, a representative diameter may range from about 0.15 mm to about 0.75 mm. For endoscopic applications, a representative diameter may range from about 0.5 mm to about 3 mm.

Cable flexibility may be varied, for instance, by the type and weave of cable materials or by physical or chemical treatments. Usually, cable stiffness or flexibility will be modified according to that required by the intended application of the articulating mechanism. The cables may be individual or multi-stranded wires made from material, including but not limited to biocompatible materials such as nickel-titanium alloy, stainless steel or any of its alloys, superelastic alloys, carbon fibers, polymers, e.g., poly (vinylchloride), polyoxyethylene, polyethylene terephthalate and other polyesters, polyolefin, polypropylene, and copolymers thereof; nylon; silk; and combinations thereof, or other suitable materials known in the art.

The cables may be affixed to the links according to ways known in the art, such as by using an adhesive or by brazing, soldering, welding, and the like, including methods described in pending and co-owned U.S. application Ser. No. 10/444,769, incorporated herein by reference in its entirety. In the embodiment depicted in FIG. 5, cable 134 is secured to link 122B by set screws 143.

Spacer links, i.e., links not connected by discrete sets of cables, may also be included in the link systems and articulating mechanisms of the invention. These links act as passive links that are not independently actuatable, but do allow for pass through of cable sets to neighboring active links. Spacer links can be desirable for providing additional length in a link system or articulating mechanism. In addition the inclusion of spacer links at one end of the mechanism allows for the proportional scaling of movement or motion of the corresponding other end. For example, the inclusion of spacer links at the proximal end of an articulating mechanism in which distal and proximal pairs of links are connected would require a more exaggerated movement by the user at the proximal end to achieve the desired motion at the distal end. This is advantageous in situations where fine, delicate controlled movements were desired, such as, for example, situations where there is a risk that a user may not possess the necessary dexterity to perform the desired procedure absent such proportional scaling of the distal end movement or motion. Alternatively, spacer links can be provided on the distal end, in which case the degree of distal end movements would be proportionally greater than those of the proximal end, which may also be desirable for particular applications. In addition to the above, proportional scaling of movement or motion can also be accomplished by increasing or decreasing the radius or distance that the cable channels are located from the center axis, as further described.

Figure 1B:
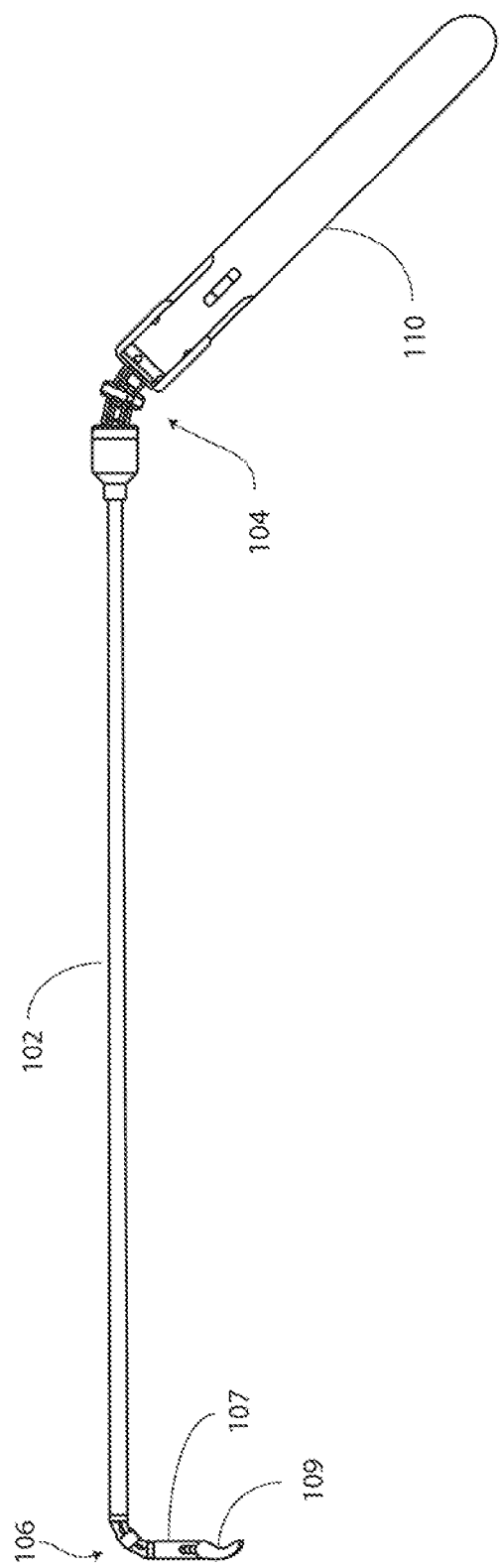
FIG. 1B shows a top view of the embodiment of FIG. 1A, with the device articulated into a different position.

Turning to the embodiment of FIGS. 1A and 1B, the configuration of the proximal and distal links is such that movement of proximal link set 104 causes amplified movement in distal link set 106. With particular reference to FIGS. 4 and 5, it can be seen that proximal links 122B, 124B and 126B are generally larger than their distal counterparts 122A, 124A and 126B. More importantly, the radius or distance that the cable channels (138B) are located from the center axis of the corresponding links is greater for proximal links 122B, 124B and 126B relative to their distal link counterparts (138A). As a result of this difference, the given link pairs when manipulated exhibit reciprocal movement that is proportional to this difference. For any two link pairs, the difference can be expressed in terms of the resulting pivot angle that results when the links are manipulated relative to their unpivoted state. Thus, for any given link pair $L_1$ and $L_2$ having differing cable channel location radii of $R_1$ and $R_2$, respectively, and where $R_2 > R_1$, when $L_1$ is pivoted to an angle of $A_1$, corresponding link $L_2$ will have a resulting pivot angle $A_2 = A_1 \times \sin^{-1}(R_1/R_2)$. An increase or decrease of cable channel location radii can therefore proportionally increase or decrease the bend angle of corresponding proximal and distal link systems. This can have important ergonomic applications, including in surgical application where a smaller angle of flex at the user operating, proximal end can result in a greater angle of flex or bend at the distal end, allowing for exaggerated or increased movement of the distal end to deploy and/or actuate surgical tools or instruments. This can be seen with particular reference to FIG. 1B, which shows the link sets 104 and 106 of device 100 in a bent configuration. The angle of movement of needle driver 107 at the end of distal link set 106 relative to elongate shaft 112 is approximately 90 degrees, and proportionally greater than the angle of handle 110 at the proximal end of proximal link set 104 relative to the shaft, which as shown is approximately 45 degrees.

In the embodiment shown in FIGS. 1 and 3-6, handle 110 is affixed to the proximal end of proximal link set 104. In this configuration, the handle itself can be used to manipulate the proximal links thereby resulting in corresponding manipulation of the distal links. Thus the handle itself can be used to manually manipulate and steer the distal end needle driver. In an alternative embodiment depicted in FIG. 8, needle driver 700 includes handle 710 which is directly affixed to the proximal end of elongate shaft 712. Proximal link set 704 is operably connected to distal link set 706 as before, but associated link cables are routed such that link set 704 emerges from the handle itself with the distal-most link of the link set being secured to the handle. In this configuration, the handle can manipulate or direct the elongate shaft. The proximal link set then is separately manipulated in order to steer distal end needle driver tool 707, similar to a joystick. This "joystick" configuration can provide increased control by the user in certain orientations or uses.

The linking systems, articulating mechanisms, and devices incorporating such systems or mechanisms may also include a locking mechanism. When activated, the locking mechanism prevents one or more links or pairs of links from moving. In one aspect, the locking mechanism is configured to receive the cables (or other like actuating elements) that connect to and manipulate the links and, when activated, restrict cable (or other like actuating element) movement thereby restricting and locking corresponding connected link pairs. In certain variations, the locking mechanism includes moveable locking members and a fixed contact member, such that movement of the moveable locking members brings the cables (or other like actuating elements) into contact with the fixed contact member, impeding further movement of the cables (or other like actuating elements) and thereby also impeding movement of the links. The locking mechanism described are compatible with the links and link systems disclosed herein as well as other link systems, including those described e.g. in pending and co-owned U.S. application Ser. No. 10/444,769, incorporated herein by reference in its entirety, as well as other known link systems.

FIGS. 9-12 show an embodiment of one such locking mechanism. With particular reference to FIG. 11A-11B, locking mechanism 300 includes an axially aligned fixed collar 302 and an axially aligned moveable collar 304 within housing 305. The inner surface of fixed collar 302 and the outer surface of moveable collar 304 are tapered such that moveable collar 304 can be partially received within fixed collar 302 as depicted. Pin 312 extends from moveable collar 304 through slot 314 in housing 305. Lever 310 is pivotally connected to housing 305 at pivot 316, with cam 318 in contact with pin 312. Cables 309 and 308 are aligned along the longitudinal axis of the mechanism. The cable are further received through fixed collar 302 and then deployed around the perimeter moveable collar 304. In the unlocked position, as shown in FIGS. 9B, 11B and 12B, lever 310 is in the upright position, approximately perpendicular to axis of the mechanism. In this position, there is sufficient clearance between the two collars to allow the cables to freely translate through the mechanism with minimal frictional contact between fixed collar 302 and movable collars 304, as is shown most clearly in FIG. 12B.

In the locked position, as depicted in FIGS. 9A-11A, lever 310 is pivoted downward until approximately parallel to the central axis of the locking mechanism. This movement causes cam 318 to engage and translate pin 312 and thus collar 304 toward collar 302. When the lever in the locked position, the pin engages detent 319, maintaining the lever in the locked position. As a result of such movement collar 304 toward collar 302, the cables come into frictional contact with the collars and are in essence pinched between the two collars, thereby frictionally impeding further movement of the cables and thus also impeding movement of links connected to the cable.

FIGS. 13-18 show another embodiment of a locking mechanism according to the invention. In this embodiment, locking mechanism 400 includes housing 402 with channels that receive cables. As will be appreciated, the housing can be incorporated into the shaft portion or elsewhere along an articulating mechanism. Alternatively the shaft portion itself can form the housing. Slider 410 surrounds housing 402 and is moveable relative to the housing in an axial direction. Housing 402 also includes a central channel 408 running along the central axis of the cylinder. The slider moves in the direction of the central axis to activate the locking mechanism, as is further described. FIGS. 17A and 18A show top and cross-sectional views, respectively, of the axial slider mechanism in the unlocked position. With reference to FIG. 18A, the housing includes two locking channels 414 and 416 disposed at different positions with respect to the central axis of housing 402. Button members 418 and 424 are disposed in locking channels 414 and 416, respectively. Each button member includes a head (421, 427), spring (420, 426) and a cable contact element (422, 428). With reference to button member 418, cable contact element 422 is positioned in channel 414 perpendicular to the central axis and in proximity to cable 432 as it passes through channel 436. Spring 426 has sufficient expansive force to maintain contact element 422 in light contact with the cable and head 421 in contact with the interior of slider 410, while still allowing cable 432 to pass freely through channel 436 with minimum resistance. Button member 424 is similarly situated in channel 416 and similarly oriented relative to cable 434 as it passes through channel 438.

Figure 18A:
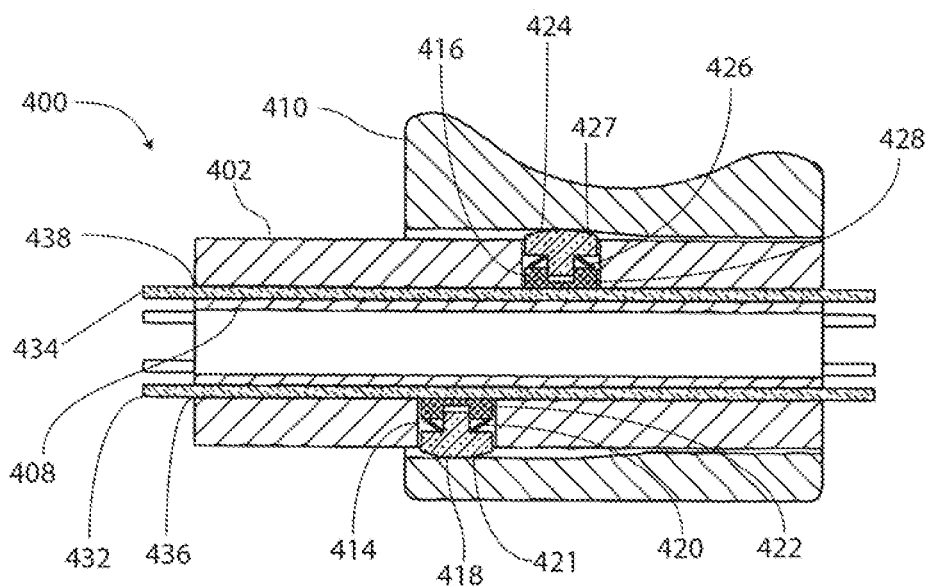
FIGS. 18A-18C show cross-sectional views of the locking mechanism depicted in FIG. 17A-C, respectively, taken along planes designated by lines 18A-18A, 18B-18B, and 18C-18C, respectively.
Figure 18B:
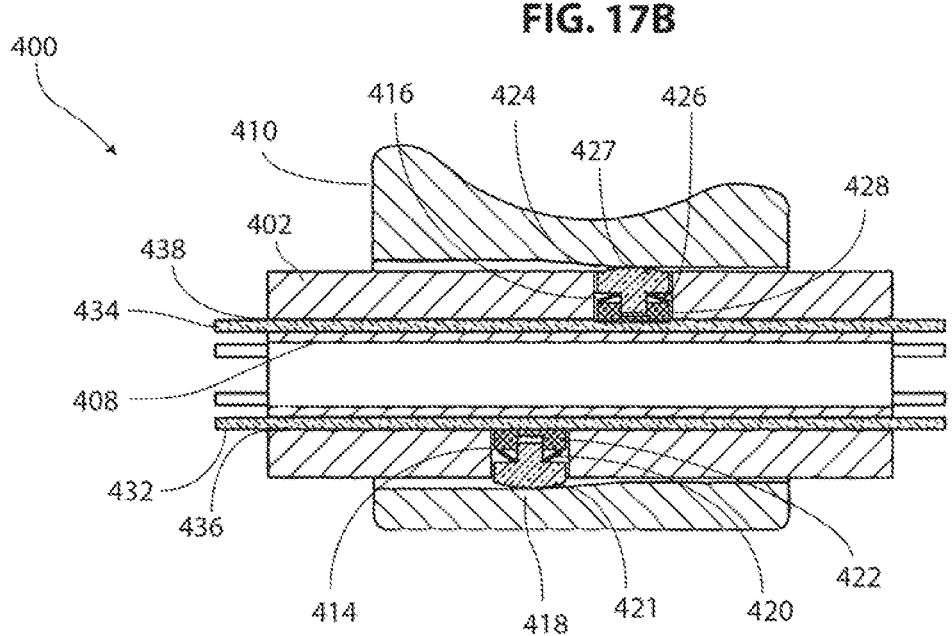
Figure 18C:
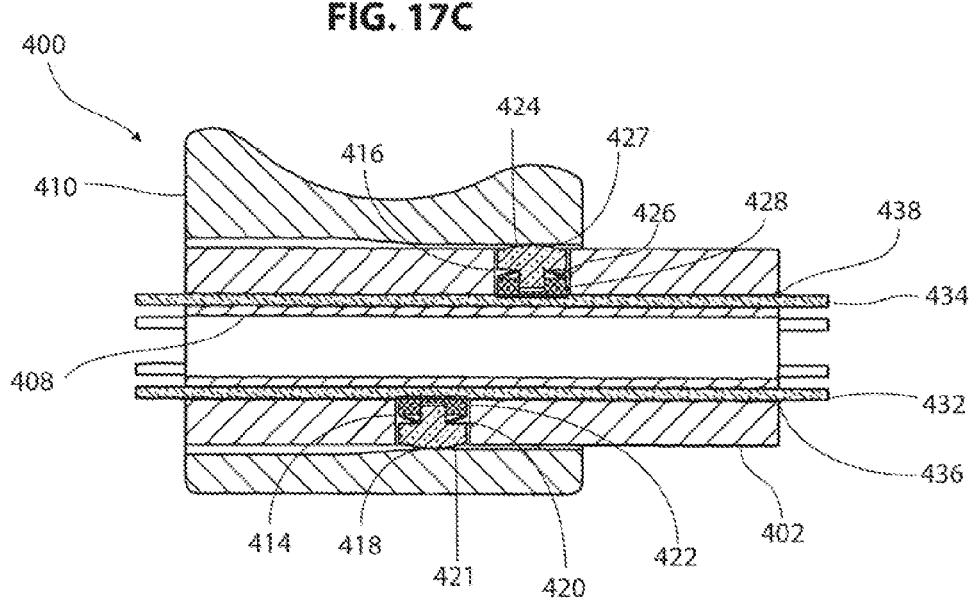

As seen most clearly in FIGS. 18A-18C, slider 410 includes areas where the inner diameter of the slider is larger such that there is a gap between the slider and housing 402, as well as areas where inner diameter of the slider is smaller such that there is only a small clearance between the slider and the housing. These areas are aligned linearly to coincide with the locking channels. When the axial slider mechanism 400 is in the fully unlocked position (FIGS. 17A and 18A), the slider 410 is positioned such that the gap areas are aligned with both locking channels 414 and 416. In the fully unlocked position, neither button member exerts sufficient force against the respective associated cable to frictionally impede movement of the cables. The cables (432, 434) are thus free to translate in their respective through-channels (436, 438), resulting in corresponding movement of any attached link system (not shown).

Figure 17B:
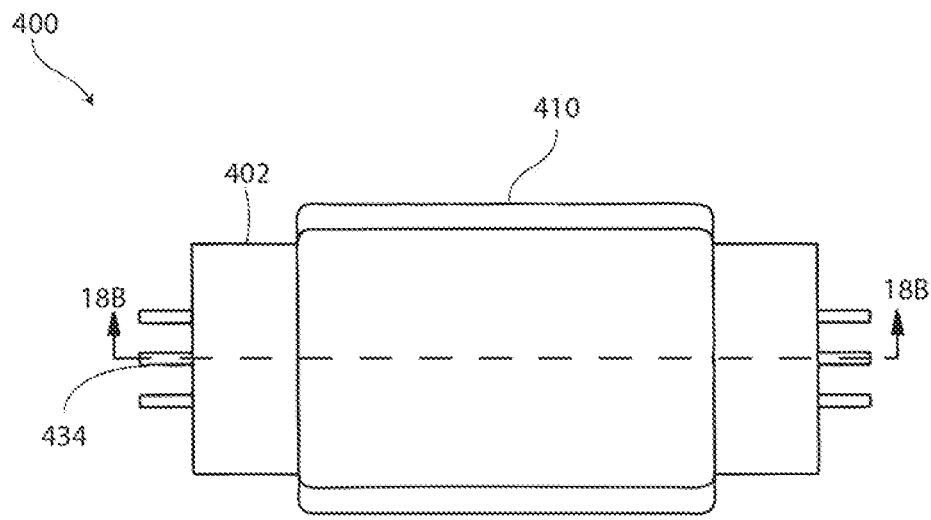

The locking mechanism 400 is activated by moving the slider 410 in the along the axis of the locking mechanism 400. FIGS. 17B and 18B show mechanism 400 in a partially locked position, where cable 434 is locked, but cable 432 is still free to translate. With reference to FIG. 18B, it can be seen that slider 410 has now been positioned such that at area of minimal clearance now coincides with locking channel 416. As a result, the slider exerts increased radial force against head 427 of button member 424 along locking channel 416 that overcomes the expansive force of spring 426 such that cable contact member 428 is pressed against cable 434 with increased force and into frictional contact with the inside wall of channel 438. Further translational movement of cable 434 is impeded, as thus is any further movement of a link or links (not shown) connected to cable 434. In this same configuration however, slider 410 continues to have a gap area coinciding with locking channel 414, such that cable 432 remains free to translate within through-channel 436, and thus a link or links (not shown) associated with cable 432 remain moveable. The net result is that translational movement of cable 434 is frictionally impeded, but movement of cable 432 is unimpeded, thereby partially locking an associated link system (not shown).

Figure 17C:
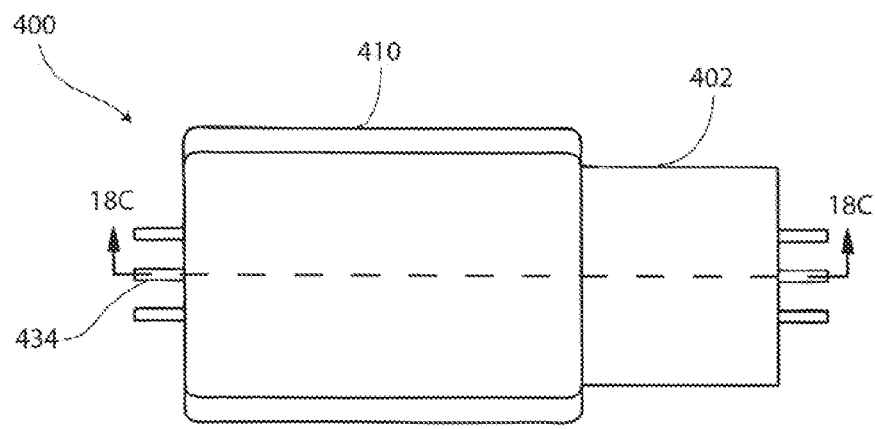

FIGS. 17C and 18C show locking mechanism 400 in the fully locked position. With reference to FIG. 18C, the slider 410 is positioned with areas of minimal clearance coinciding with both locking channels 414 and 416, such that both cable contact elements (422, 428) button members (418, 424) are pressed against their respective cables (432, 434) bringing the cables into frictional contact with the inner walls of their respective through channels (436, 438), thereby frictionally impeding translational movement of both cables and any associated links. As can be appreciated from this embodiment, different links or pairs of links connected by separate sets of cables can have locking channels associated with each set that are oriented radially about a specified position along the housing axis. As the slider is moved axially relative to the housing, these links or pairs of links can be sequentially locked or unlocked. The ability to sequentially lock or unlock the connected links or link pairs can be advantageous, for example, in situations were it is desirable to lock portions of the link systems in place while other portions remain free for further steering, navigation, direction, or actuation of a distal tool or instrument. Further, not all cables of a link set need be restrained for effective locking of connected link pairs. For example, for cable sets having three cables, only two need be restrained for effective locking.

Figure 19:
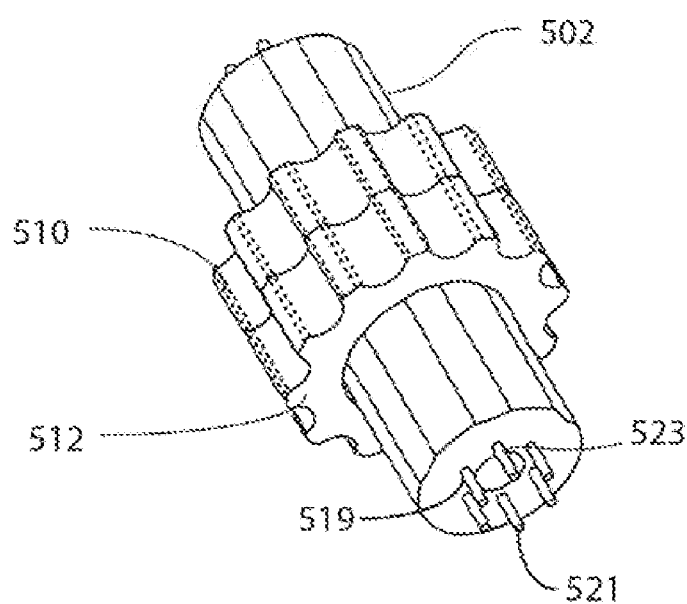
FIG. 19 shows a perspective view of a link locking mechanism, according to yet another embodiment depicted in the invention.
Figure 20A:
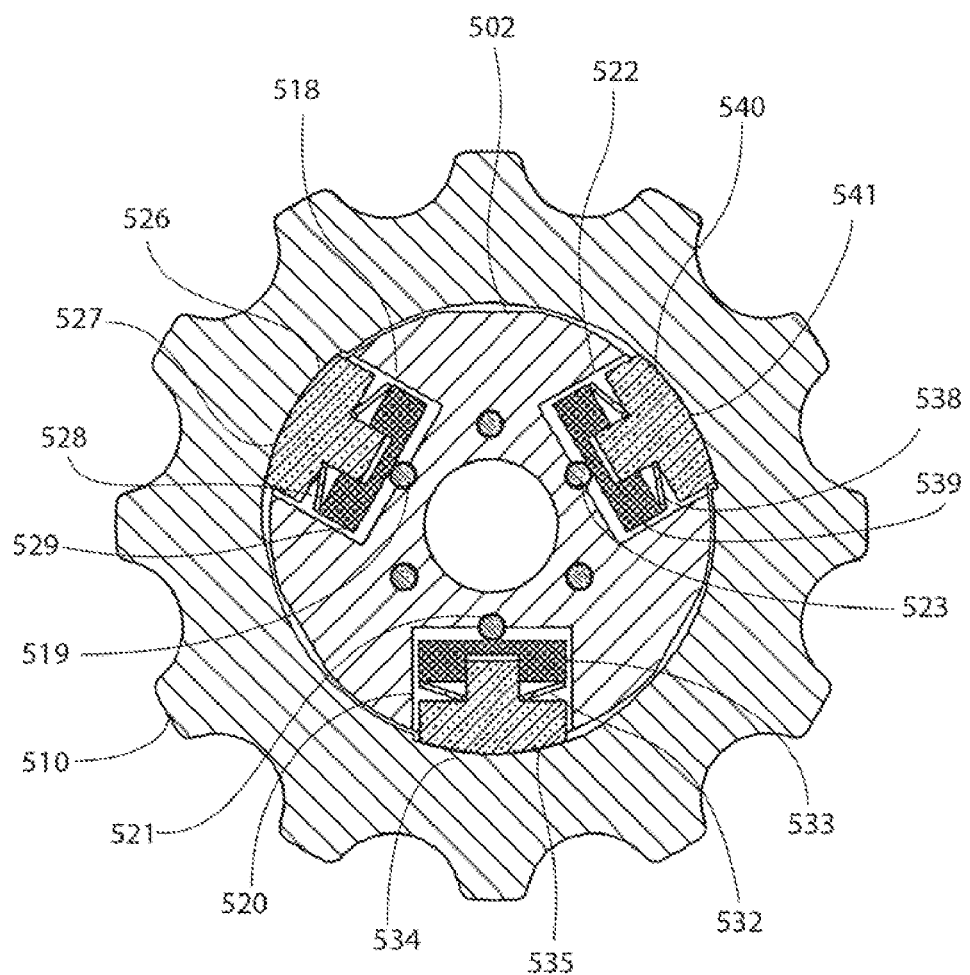
FIGS. 20A and 20B show cross-sectional views taken perpendicular to the longitudinal axis of the mechanism of FIG. 19 in locked (20B) and unlocked (20A) conformations, respectively.
Figure 20:
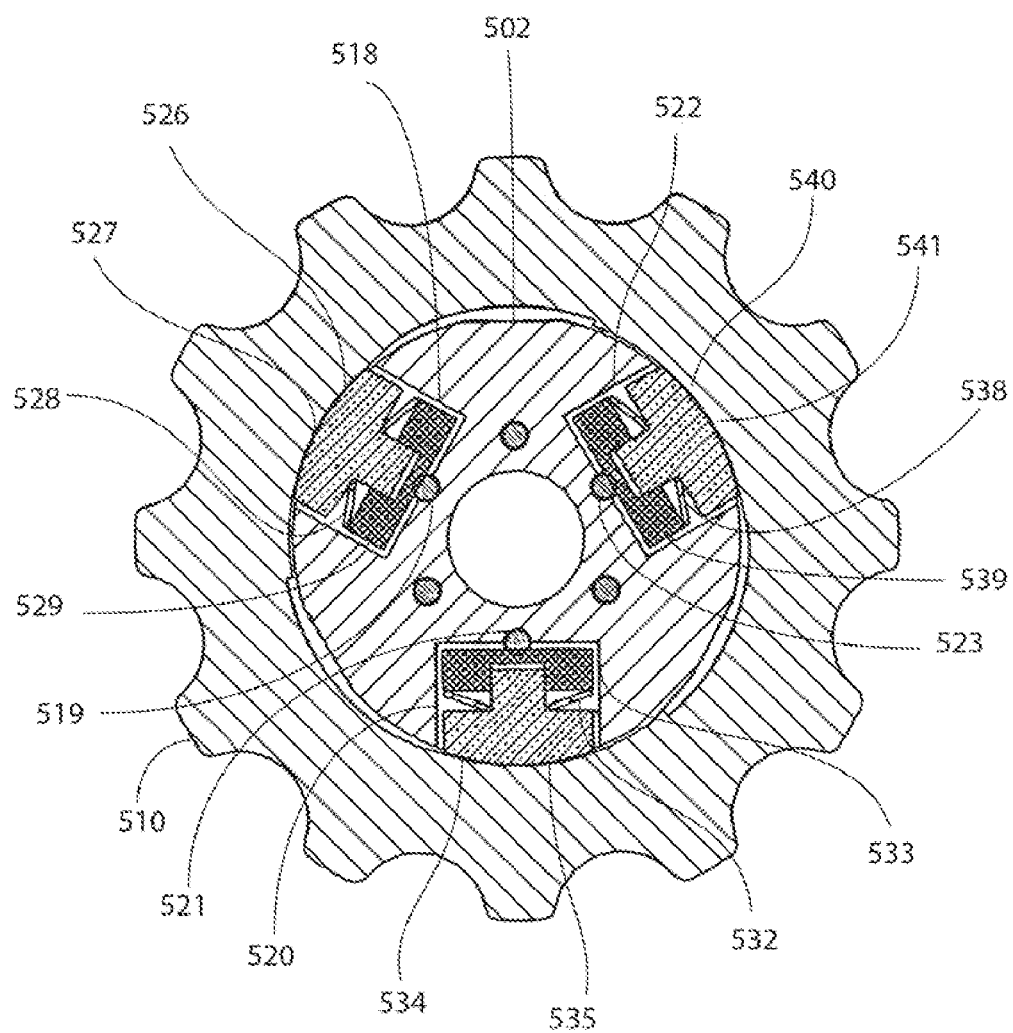

In further embodiment of a locking mechanism according to the invention is depicted in FIGS. 19-20. Locking mechanism 500 includes cylindrical housing 502 surrounded by co-axial locking rings 510 and 512. Locking rings 510 and 512 are rotatable around housing 502, and function similar to slider 410 in the embodiment of FIGS. 13-18. When locking rings 510 and 512 are rotated to specific positions, one or more cables that are received through housing 502 are prevented from moving. Again, the housing itself can be integrated into the shaft portion of an articulating mechanism, or elsewhere along the mechanism, or the shaft portion itself can form the housing.

FIGS. 20A and 20B show locking mechanism 500 in unlocked (FIG. 20A) and locked (FIG. 20B) conformations with respect to cables 519, 521, 523. Housing 502 is surrounded by coaxial locking ring 510. The interior of locking ring 510 and the exterior perimeter of cylinder does not have a uniform matching diameter but rather have sections with tapered gaps interspersed by sections with only minimal clearance between the two. Cylinder 502 includes three locking channels 518, 520, and 522 disposed at various positions radially about the cylinder 502. Each locking channel (518, 520, 522) is associated with a cable through channel that receives an associated cable (519, 521, 523). It will be appreciated that the remaining depicted cables will be associated with locking rings and channels in different axial locations along the housing. The button members are similarly configured and in their respective channels as are those of the FIGS. 13-18 embodiment, with each button member (526, 534, 540) having a head (527, 535, 541), spring (528, 532, 538), and cable contact member (529, 533, 539). With further reference to FIG. 20A, when the locking mechanism is in the unlocked configuration, the locking ring 510 is positioned so that each of the button members (526, 534, 540) is aligned with a gapped area, such that none of the buttons is depressed with sufficient force to move the associated cables (519, 521, 523) into frictional contact with the inner walls of their respective through channels so as to impede cable movement. Thus, in this unlocked position the cables (519, 521, 523) are free to translate through cylinder 502.

FIG. 20B shows the mechanism moved into a locked configuration by rotating locking ring 510 around cylinder 502. When the locking ring 510 is rotated to the locked configuration, each of the buttons (526, 534, 540) now coincides with an area of minimal clearance between locking ring 510 and cylinder 502. Much like in the embodiment of FIGS. 13-19, this similarly results in each of the buttons (526, 534, 540) being depressed into the locking channels with sufficient force to overcome associated spring members (528, 532, 538) and push their associated cable contact members (529, 533, 539) radially against their associated cables (519, 521, 523), bringing the associated cables into frictional contact with the inner wall of their associated through channels. In this manner, cables (519, 521, 523) are frictionally impeded from further translational movement through cylinder 502, thereby locking the cables and any links connected to the cables in place. As can be appreciated from this embodiment, different links or pairs of links connected by separate sets of cables can again have locking channels associated with each set that are oriented radially about a specified position along the cylinder that is associated with a single locking ring. Each of these links or link pairs can thus be independently locked or unlocked. The ability to independently lock or unlock the connected links or link pairs can have many advantages, including as previously mentioned situations were it is desirable to lock portions of the link systems in place while other portions remain free for further steering, navigation, direction, or actuation of a distal tool or instrument.

Locking mechanisms may be of any size and shape, as the purpose dictates, but their size and shape is typically similar to that of any associated link system, articulating mechanism, or device incorporating such systems or articulating mechanisms. Like the link systems themselves, the locking mechanisms are generally but need not be cylindrical, and may include channels for passage of the cables that connect the locking mechanism to other components of a device, as well as additional cables, wires, fiberoptics or other like elements associated with a desired tool or instrument used in conjunction with the locking mechanism. In embodiments of the locking mechanism that include cables, cable channel diameters are usually slightly larger than the cable diameters, creating a slip fit. Further, the locking mechanisms may also include one or more channels for receiving elements of attachable surgical instruments or diagnostic tools or for passage of cables that actuate them.

In some embodiments, a locking mechanism may be disposed on one end of a linking system or articulating mechanism. In other embodiments, the locking mechanism may be disposed at any position at the proximal or distal end of the surgical instrument. Although the many locking mechanisms that have been illustrated in the accompanying figures have certain configurations number components, this is solely for the illustrative purpose of indicating the relationship of the components to one another. Any number of components may be employed, depending on such factors as the intended use of the locking mechanism.

The invention also contemplates kits for providing various linking systems, articulating mechanisms, locking mechanisms, and associated accessories. For example, kits containing linking systems and articulating mechanisms having different lengths, different segment diameters, and/or different types of tools or instruments may be provided. The kits may optionally include different types of locking mechanisms. The kits may be further be tailored for specific applications. For example, kits for surgical applications can be configured for, e.g., endoscopy, retraction, or catheter placement, and/or for particular patient populations, e.g., pediatric or adult.

We claim:

1. An articulating mechanism for remote manipulation of a surgical or diagnostic tool comprising:
   multiple pairs of links, each link being a discrete portion of the mechanism that is capable of movement relative to another discrete portion of the mechanism, each of the links being generally aligned along a common central longitudinal axis, each pair having a link in a proximal link set being maintained in a spaced apart relationship relative to the other link of the pair in a distal link set, all of the links in the proximal link set being located proximally from all of the links in the distal link set, a proximal most active link of the proximal link set forming a link pair with the distal most active link of the distal link set, a distal most active link of the proximal link set forming a link pair with the proximal most active link of the distal link set, and any intervening active links following this same link pair ordering, and wherein at least two adjacent links are pivotable relative to one another about two distinct, independently pivotable, longitudinally spaced pivot points, wherein each of the pivot points has a pivot axis that generally passes through the central longitudinal axis; and
   multiple sets of cables, each set dedicated to connecting the links of a discrete pair to one another such that movement of one link of a pair causes corresponding relative movement of the other link of the pair directly through cable movement.

2. The articulating mechanism of claim 1 wherein the at least two adjacent links have opposed surfaces each having an axially aligned convex protrusion or concave depression, and wherein the at least two adjacent links are separated by a bushing interposed between the at least two adjacent links, the bushing contacting the convex protrusion or concave depression of each of the at least two adjacent links.

3. The articulating mechanism of claim 2 wherein at least one convex protrusion or concave depression of adjacent links is hemispherical.

4. The articulating mechanism of claim 2 wherein the bushing has a concave depression and/or a convex protrusion that receives the convex protrusion or concave depression of each of the at least two adjacent links.

5. The articulating mechanism of claim 4 wherein the at least one bushing has two convex protrusions on opposite sides.

6. The articulating mechanism of claim 2 further comprising one or more spacer links that are not connected by discrete sets of cables and wherein each spacer link includes an axially aligned convex protrusion or a concave depression, and is separated from an adjacent link by a bushing interposed between the spacer link and adjacent link.

7. The articulating mechanism of claim 6, wherein the convex protrusion or a concave depression of the spacer link is hemispherical.

8. The articulating mechanism of claim 1 wherein the links form proximal and distal ends with links of corresponding pairs being located on the proximal and distal ends respectively and where movement of the proximal end results in corresponding relative movement of the distal end.

9. The articulating mechanism of claim 8 wherein said corresponding relative movement of the distal end is reciprocal to the movement of the proximal end.

10. The articulating mechanism of claim 8 wherein said corresponding relative movement of the distal end mirrors the movement of the proximal end.

11. The articulating mechanism of claim 8 wherein a surgical or diagnostic tool is attached to the distal end.

12. The articulating mechanism of claim 11 wherein the tool is selected from the group consisting of a stapler, clamp, grasper, scissors, cutter, an ablation element, and a cauterizing element.

13. The articulating mechanism of claim 1 further comprising an elongate shaft disposed between the pairs of links that maintain the pairs of links in a spaced apart relationship.

14. The articulating mechanism of claim 13 wherein the elongate shaft accommodates the sets of cables.

15. The articulating mechanism of claim 1, wherein pairs of links include channels for receipt and passage of sets of cables associated with adjacent pairs of links.

16. The articulating mechanism of claim 1 further comprising one or more spacer links that are not connected by discrete sets of cables.

17. The articulating mechanism of claim 1 wherein the cables connecting a pair of links are at a different radial distance from the center of the first link of the pair as compared to the second link of the pair.

18. The articulating mechanism of claim 1 wherein at least one set of the cables passes at least partially through both of the adjacent links and spans a gap there between, wherein each of the two adjacent links includes a cable exit point where one of the cables emerges from the link and into the gap between the links, wherein at least one of the two distinct pivot points is situated such that it is substantially longitudinally aligned with one of the cable exit points that is on one of the two adjacent links to create a generally neutral bias in the cable.

19. The articulating mechanism of claim 18 wherein one of the two distinct pivot points is situated such that it is substantially longitudinally aligned with the cable exit point that is on one of the two adjacent links, and the other of the two distinct pivot points is situated such that it is substantially longitudinally aligned with the cable exit point that is on the other of the two adjacent links to create a generally neutral bias in the cable.

20. The articulating mechanism of claim 1 wherein at least one set of the cables passes at least partially through both of the adjacent links and spans a gap there between, wherein each of the two adjacent links includes a cable exit point where one of the cables emerges from the link and into the gap between the links, wherein at least one of the two distinct pivot points is situated such that it is substantially longitudinally between the cable exit points that are on the two adjacent links to create a generally negative bias in the cable.

21. The articulating mechanism of claim 20 wherein both of the two distinct pivot points are situated such that they are substantially longitudinally between the cable exit points that are on the two adjacent links to create a generally negative bias in the cable.

22. The articulating mechanism of claim 1 wherein at least one set of the cables passes at least partially through both of the adjacent links and spans a gap there between, wherein each of the two adjacent links includes a cable exit point where one of the cables emerges from the link and into the gap between the links, wherein at least one of the two distinct pivot points is situated such that it is substantially longitudinally on an opposite side of one of the cable exit points from the gap between the links to create a generally positive bias in the cable.

23. The articulating mechanism of claim 22 wherein one of the two distinct pivot points is situated such that it is substantially longitudinally on an opposite side of one of the cable exit points from the gap, and the other of the two distinct pivot points is situated such that it is substantially longitudinally on an opposite side of the other cable exit point from the gap to create a generally positive bias in the cable.

24. A surgical instrument comprising: a surgical or diagnostic tool; a plurality of links proximal of the surgical or diagnostic tool and generally aligned along a longitudinal axis of the instrument, each link being a discrete portion of the instrument that is capable of movement relative to another discrete portion of the instrument, wherein at least two adjacent links are pivotable relative to one another about two distinct pivot points, the two pivot points being longitudinally spaced apart by at least one generally rigid member such that their relative spacing is fixed, the longitudinal axis passing through the two pivot points; an elongate shaft proximal of the plurality of links; and one or more cables distally connected to one or more links and received proximally through the elongate shaft, such that movement of one or more cables causes movement of one or more links.

25. The surgical instrument of claim 24 wherein the at least two adjacent links have opposing surfaces each having an axially aligned convex protrusion or concave depression, and wherein the at least two adjacent links are separated by a bushing interposed between the at least two adjacent links, the bushing complementing the convex protrusion or concave depression of each of the at least two adjacent links.

26. The surgical instrument of claim 25 wherein the convex protrusions and/or concave depressions of each of the at least two adjacent links is hemispherical.

27. The surgical instrument of claim 25 wherein the bushing has a concave depression and/or a convex protrusion that receive the convex protrusions and/or concave depressions of each of the adjacent links.

28. The surgical instrument of claim 24, further comprising: multiple pairs of links, each link being maintained in a spaced apart relationship on an opposite side of the shaft relative to the other link of the pair; multiple sets of cables, each set connecting the links of a discrete pair to one another such that movement of one link of a pair causes corresponding relative movement of the other link of the pair, and wherein the cables connecting at least one discrete pair of links are at a different radial distance from the center of the first link of the pair as compared to the second link of the pair.

29. The surgical instrument of claim 24, further comprising: a plurality of reciprocal links proximal of the shaft, each reciprocal link connected by at least one set of cables to one of the plurality of links distal of the shaft to form a link pair, such that movement of one link of the pair causes corresponding relative movement of the other link of the pair, wherein a proximal most active link of the links proximal of the shaft forms a link pair with the distal most active link of the links distal of the shaft, a distal most active link of the links proximal of the shaft forming a link pair with the proximal most active link of the of the links distal of the shaft, and any intervening active links following this same link pair ordering.

30. The surgical instrument of claim 29 further comprising an actuation handle proximal of the elongate shaft and operably connected to the surgical or distal tool.

31. The surgical instrument of claim 30 wherein the actuation handle is proximal of the plurality of reciprocal links.

32. The surgical instrument of claim 30 further comprising a cable locking mechanism configured to impede movement of one or more cables, thereby impeding movement of the links.

33. The surgical instrument of claim 30 wherein the cables connecting a pair of links are at a different radial distance from the center of the first link of the pair as compared to the second link of the pair.

34. A surgical instrument comprising:

a surgical or diagnostic tool;

a plurality of links proximal of the surgical or diagnostic tool and generally aligned along a longitudinal axis of the instrument, each link being a discrete portion of the instrument that is capable of movement relative to another discrete portion of the instrument, wherein at least two adjacent links are pivotable relative to one another about two distinct pivot points, the two pivot points being longitudinally spaced apart by at least one generally rigid member such that their relative spacing is fixed, each pivot point having a pivot axis that generally passes through the longitudinal axis;

an elongate shaft proximal of the plurality of links;

one or more cables distally connected to one or more links and received proximally through the elongate shaft, such that movement of one or more cables causes movement of one or more links; and a plurality of reciprocal links proximal of the shaft, each reciprocal link connected by at least one set of cables to one of the plurality of links distal of the shaft to form a link pair, such that movement of one link of the pair causes corresponding relative movement of the other link of the pair, wherein a proximal most active link of the links proximal of the shaft forms a link pair with the distal most active link of the links distal of the shaft, a distal most active link of the links proximal of the shaft forming a link pair with the proximal most active link of the of the links distal of the shaft, and any intervening active links following this same link pair ordering.

35. The surgical instrument of claim 34 further comprising an actuation handle proximal of the elongate shaft and operably connected to the surgical or distal tool.

36. The surgical instrument of claim 35 wherein the actuation handle is proximal of the plurality of reciprocal links.

37. The surgical instrument of claim 35 further comprising a cable locking mechanism configured to impede movement of one or more cables, thereby impeding movement of the links.

38. The surgical instrument of claim 35 wherein the cables connecting a pair of links are at a different radial distance from the center of the first link of the pair as compared to the second link of the pair.

39. An articulating mechanism for remote manipulation of a surgical or diagnostic tool comprising:

multiple pairs of links, each link being a discrete portion of the mechanism that is capable of movement relative to another discrete portion of the mechanism, each link being generally aligned along a common central longitudinal axis, each link being maintained in a spaced apart relationship relative to the other link of the pair, each pair having one link in a proximal link set and one link in a distal link set, a proximal most active link of the proximal link set forming a link pair with the distal most active link of the distal link set, a distal most active link of the proximal link set forming a link pair with the proximal most active link of the distal link set, and any intervening active links following this same link pair ordering, and wherein at least two adjacent links are pivotable relative to one another about two distinct pivot points, the two pivot points being longitudinally spaced apart by at least one generally rigid member, each of the pivot points having a pivot axis that generally passes through the central longitudinal axis; and multiple sets of cables, each set connecting the links of a discrete pair to one another such that movement of one link of a pair causes corresponding relative movement of the other link of the pair.

40. The articulating mechanism of claim 39 wherein the at least two adjacent links have opposed surfaces each having an axially aligned convex protrusion or concave depression, and wherein the at least one generally rigid member comprises a bushing interposed between the at least two adjacent links, the bushing contacting the convex protrusion or concave depression of each of the at least two adjacent links.

41. The articulating mechanism of claim 40 wherein at least one convex protrusion or concave depression of adjacent links is hemispherical.

42. The articulating mechanism of claim 40 wherein the bushing has a concave depression and/or a convex protrusion that receives the convex protrusion or concave depression of each of the at least two adjacent links.

43. The articulating mechanism of claim 42 wherein the bushing has two convex protrusions on opposite sides.

44. The articulating mechanism of claim 40 further comprising one or more spacer links that are not connected by discrete sets of cables and wherein each spacer link includes an axially aligned convex protrusion or a concave depression, and is separated from an adjacent link by a bushing interposed between the spacer link and adjacent link.

45. The articulating mechanism of claim 44, wherein the convex protrusion or a concave depression of the spacer link is hemispherical.

46. The articulating mechanism of claim 39 wherein the links form proximal and distal ends with links of corresponding pairs being located on the proximal and distal ends respectively and where movement of the proximal end results in corresponding relative movement of the distal end.

47. The articulating mechanism of claim 46 wherein said corresponding relative movement of the distal end is reciprocal to the movement of the proximal end.

48. The articulating mechanism of claim 46 wherein said corresponding relative movement of the distal end mirrors the movement of the proximal end.

49. The articulating mechanism of claim 46 wherein a surgical or diagnostic tool is attached to the distal end.

50. The articulating mechanism of claim 49 wherein the tool is selected from the group consisting of a stapler, clamp, grasper, scissors, cutter, an ablation element, and a cauterizing element.

51. The articulating mechanism of claim 39 further comprising an elongate shaft disposed between the pairs of links that maintain the pairs of links in a spaced apart relationship.

52. The articulating mechanism of claim 51 wherein the elongate shaft accommodates the sets of cables.

53. The articulating mechanism of claim 39, wherein pairs of links include channels for receipt and passage of sets of cables associated with adjacent pairs of links.

54. The articulating mechanism of claim 39 further comprising one or more spacer links that are not connected by discrete sets of cables.

55. The articulating mechanism of claim 39 wherein the cables connecting a pair of links are at a different radial distance from the center of the first link of the pair as compared to the second link of the pair.

* * * * *

UNITED STATES PATENT AND TRADEMARK OFFICE
CERTIFICATE OF CORRECTION

| | | |
|---|---|---|
| PATENT NO. | : 7,828,808 B2 | Page 1 of 1 |
| APPLICATION NO. | : 10/928479 | |
| DATED | : November 9, 2010 | |
| INVENTOR(S) | : Hinman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Twenty-fifth Day of January, 2011

David J. Kappos
*Director of the United States Patent and Trademark Office*